US005939525A

United States Patent [19]
McFadden et al.

[11] Patent Number: 5,939,525
[45] Date of Patent: Aug. 17, 1999

[54] METHODS OF TREATING INFLAMMATION AND COMPOSITIONS THEREFOR

[75] Inventors: D. Grant McFadden; Alexandra Lucas, both of Edmonton, Canada

[73] Assignee: Viron Therapeutics, Inc., London, Canada

[21] Appl. No.: 08/411,043

[22] Filed: Mar. 27, 1995

[51] Int. Cl.$^6$ .................................................. A61K 38/16
[52] U.S. Cl. ............................................ 530/324; 514/21
[58] Field of Search ................................ 514/21; 530/324

[56] References Cited

FOREIGN PATENT DOCUMENTS

| 0 567 816A1 | 11/1993 | European Pat. Off. . |
| WO 92/06706 | 4/1992 | WIPO . |
| WO 92/22320 | 12/1992 | WIPO . |
| WO 93/10812 | 6/1993 | WIPO . |
| WO 95/27503 | 10/1995 | WIPO . |

OTHER PUBLICATIONS

Fukusen, et al. (1987) "Kinetic Studies on the Inhibitions of Mast Cell Chymase by Natural Serine Protease Inhibitors: Indications for Potential Biological Functions of These Inhibitors", *Biochemical Medicine and Metabolic Biology* 38:165–169.
Upton, Mol. & Cell. Biol., v. 6, No. 1, pp. 265–276 (Jan. 1986).
Upton, FEBS 4108, v. 207, No. 1, pp. 115–120 (Oct. 1986).
Mossman et al. (1995) "The Myxoma Virus–soluble Interferon–γ Receptor Homolog, M–T7, Inhibits Interferon–γ in a Species–specific Manner" *J. Biol. Chem.* 270 (7):3031–3038.
Lin et al. (1993) "A Novel Viral Anti–Inflammatory Protein, SERP–1, Reduces Intimal Hyperplasia in Cholesterol–Fed Rabbits after Balloon Angioplasty" 66th Scientific Session of the American Heart Association, Atlanta, GA.
Lucas et al. (1994) "A Unique Viral Anti–Inflammatory Protein, SERP–1, Reduces Intimal Hyperplasia in Cholesterol–Fed Rabbits After Angioplasty" *J. Cell. Biochem. Suppl.18A*: 286 (Abstract E 315).
Upton et al. (1990) "Myxoma Virus and Malignant Rabbit Fibroma Virus Encode a Serpin–like Protein Important for Virus Virulence" *Virology* 179:618–631.
Lomas et al. (1993) "Inhibition of Plasmin, Urokinase, Tissue Plasminogen Activator, and $C_{1S}$ by a Myxoma Virus Serine Proteinase Inhibitor" *J. Biol. Chem.* 268 (1):16–521.
Mihelcic et al. (1994) "Inhibition of Leukocyte L–Selectin Function With a Monoclonal Antibody Attenuates Reperfusion Injury to the Rabbit Ear" *Blood* 84 (7):2322–2328.
Mulligan et al. (1994) "Role of Leukocyte Adhesion Molecules in Lung and Dermal Vascular Injury After Thermal Trauma of Skin" *Am. J. Pathol.* 144 (5):1008–1015.
Hill et al. (1992) "Soluble Complement Receptor Type 1 Ameliorates the Local and Remote Organ Injury After Intestin Ischemia–Reperfusion in the Rat" *J. Immunol. 149*:5 1723–1728.
Mulligan et al. (1993) "Role of $\beta_1$, $\beta_2$ Integrins and ICAM–1 in Lung Injury After Deposition of IgG and IgA Immune Complexes" *J. Immunol.* 150 (6):2407–2417.
Mulligan et al. (1993) "Role of Leukocyte Adhesion Molecules in Complement–Induced Lung Injury" *J. Immunol.* 150 (6):2401–2406.
Pemberton et al. (1993) "Microvascular Effects of Complement Blockade with Soluble Recombinant CR1 on Ischemia/Reperfusion Injury of Skeletal Muscle" *J. Immunol. 150*:5104–5113.
Mulligan et al. (1992) "Protective Effects of Soluble CR1 in Complement– and Neutrolphil–Mediated Tissue Injury" *J. Immunol.* 148 (5): 1479–1485.
Rabinovici et al. (1992) "Role of Complement in Endotoxin/Platelet–Activating Factor–Induced Lung Injury" *J. Immunol.* 149 (5):1744–1750.
Harlan et al. (1992) "In Vivo Models of Leukocyte Adherence to Endothelium", in *Adhesion: Its Role in Inflammatory Disease*, Harlan et al., eds., W.H. Freeman and Co., New York, 117–150.
Sundberg et al. (1994) "Full–Thickness Skin Grafts from Flaky Skin Mice to Nude Mice: Maintenance of the Psoriasiform Phenotype" *J. Invest. Dermatol.* 102 (5):781–788.
Gilhar et al. (1994) "The Nude Mouse Model for the Study of Human Skin Disorders" *Dermatology 189* (1)5–8.
Penning et al. (1993) "The Design and Synthesis of Second Generation Leukotriene $B_4$ ($LTB_4$) Receptor Antagonists Related to SC–41930" *Agents Actions* Special Conference Issue 39:C11–C13.
Friedrichs et al. (1994) "Effects of Heparin and N–Acetyl Heparin on Ischemia/Reperfusion–Induced Alterations in Myocardial Function in the Rabbit Isolated Heart" *Circulation Res.* 75 (4):701–710.
Shandelya et al. (1993) "Soluble Complement Receptor Type 1 Inhibits the Complement Pathway and Prevents Contractile Failure in the Postischemic Heart" *Circulation* 88 (6):2812–2826.
Kusumoto et al. (1993) "Role of Endogenous Endothelin in Extension of Rabbit Myocardial Infarction" *J. Cardiovasc. Pharmacol.* 22 (8): S339–342.
Zierhut et al. (1994) "Pharmacological Actions of SDZ 218–135, A Novel Positive Inotropic Agent" *Cardiovasc. Drugs Ther.* 8 (2):235–244 (Abstract).

(List continued on next page.)

*Primary Examiner*—Cecilia J. Tsang
*Assistant Examiner*—Patrick R. Delaney
*Attorney, Agent, or Firm*—Scully, Scott, Murphy & Presser

[57] ABSTRACT

Compositions and methods for treating inflammatory cell infiltration in a tissue of a mammalian subject are provided. The method involves administering a therapeutically effective amount of SERP-1, SERP-1 analog or biologically active fragment thereof admixed with a pharmaceutically acceptable carrier to a subject in need of such treatment. Biologically active SERP-1 analogs are also provided. The compositions and methods of the present invention are useful for treating numerous inflammatory based diseases and injuries.

4 Claims, 15 Drawing Sheets

OTHER PUBLICATIONS

Martorana et al. (1994) "Antiischemic Effects of Pirsidomine, a New Nitric Oxide Donor" *Eur. J. Pharmacol.* 257 (3):267–73.

Sun et al. (1994) "Cardiac Angiotensin Converting Enzyme and Myocardial Fibrosis in the Rat" *Cardiovacs. Res.* 28 (9):1423–1432.

Teerlink et al. (1994) "Role of Endothelin in the Maintenance of Blood Pressure in Conscious Rats with Chronic Heart Failure. Acute Effects of the Endothelin Receptor Antagonist Ro 47–0203 (Bosentan)" *Circulation* 90 (5):2510–8.

Abraham et al. (1994) "$\alpha_4$–Integrins Mediate Antigen–induced Late Bronchial Responses and Prolonged Airway Hyperresponsiveness in Sheep" *J. Clin. Invest.* 93:776–787.

Pretolani et al. (1994) "Antibody to Very Late Activation Antigen 4 Prevents Antigen–induced Bronchial Hyperreactivity and Cellular Infiltration in the Guinea Pig Airways" *J. Exp. Med.* 180:795–805.

Cosimi et al. (1990) "In Vivo Effects of Monoclonal Antibody to ICAM–1 (CD54) In Nonhuman Primates with Renal Allografts" *J. Immunol.* 144 (12):4604–4612.

Paul et al. (1993) "The Efficacy of LFA–1 and VLA–4 Antibody Treatment in Rat Vascularized Cardiac Allograft Rejection" *Transplantation* 55 (5):1196–1199.

Wilson et al. (1994) "The Effect of Low Molecular Weight Heparin on Intimal Hyperplasia in Vein Grafts" *Eur. J. Vasc. Surg.* 8 (1):60–4.

Johnstone et al. (1994) "Effects of Intraoperative Radiotherapy on Vascular Grafts in a Canine Model" *Int. J. Radiat. Oncol. Biol. Phys.* 29 (5):1015–25.

Scott et al. (1994) "Local Delivery of an Antithrombin Inhibits Platelet–Dependent Thrombosis" *Circulation* 90 (4):1951–5.

Mazur et al. (1994) "Selective $\alpha_{11b}$ $\beta_3$ Receptor Blockage with Peptide TP9201 Prevents Platelet Uptake on Dacron Vascular Grafts Without Significant Effect on Bleeding Time" *J. Lab. Clin. Med.* 124 (4):589–99.

Nakamoto et al. (1994) "In Vivo Treatment of Infected Prosthetic Graft Material With Urokinase: An Animal Model" *J. Vasc. Interv. Radiol.* 5 (4):549–52.

Kiberd et al. (1994) "Modulation of Glomerular Structure and Function in Murine Lupus Nephritis by Methyl–prednisolone and Cyclophosphamide" *J. Lab Clin. Med.* 124 (4):496–506.

Singh et al. (1994) "Interleukin–1 Contributes to High Level IgG Production in the Murine MRL/1pr Lupus Model" *Immunol. Invest.* 23 (4&5): 281–92.

Nicoletti et al. (1994) "The Effects of Thymopentin on the Development of SLE–like Syndrome in the MRL/lpr–lpr Mouse" *Scand. Journ. Immunol.* 40 (5):549–56.

Zamvil et al. (1994) "'Lupus–Prone' Mice are Susceptible to Organ–Specific Autoimmune Disease, Experimental Allergic Encephalomyelitis" *Pathobiology* 62 (3):113–9.

Lowrance et al. (1994) "Spontaneous Elaboration of Transforming Growth Factor β Suppresses Host Defense Against Bacterial Infection in Autoimmune MRL/lpr Mice" *Journ. Exp. Med.* 180 (5):1693–1703.

Ramos et al. (1994) "Differences in Non–MHC Alloantigens Promote Tissue Rejection but Fail to Mediate Allogeneic Co–operation and Autoimmunity in Mice Neonatally Injected with Semi–Allogeneic $F_1$ B Cells" *Immunology* 82 (2): 287–93.

Takahashi et al. (1994) "In Vivo Differentiation of Edematous Changes After Stroke in Spontaneously Hypertensive Rats Using Diffusion Weighted MRI" *Acta Neurochir. Suppl.* 60:224–7.

Davis et al. (1994) "The Effect of Age on Cerebral Oedema, Cerebral Infarction and Neuroprotective Potential in Experimental Occlusive Stroke" *Acta Neurochir Suppl.* 60:282–4.

Bowes et al. (1994) "Diaspirin Cross–Linked Hemoglobin Improves Neurological Outcome Following Reversible But Not Irreversible CNS Ischemia in Rabbits" *Stroke* 25 (11):2253–57 (Abstract).

Peterseim et al. (1994) "Stability of the β–Adrenergic Receptor/Adenylyl Cyclase Pathway of Pediatric Myocardium After Brain Death" *J. Heart Lung Transplant.* 13 (4):635–640.

Wishart et al. (1994) "Comparisons of Repetitive–and Single–Insult Ischaemia: Effects on Regional Brain Damage and Behaviour" *Neuroreport* 5 (12)1541–1544.

Yednock et al. (1992) "Prevention of Experimental Autoimmune Encephalomyelitis by Antibodies Against $\alpha 4\beta 1$ Integrin" *Nature* 356:63–66.

Burkly et al. (1994) "Protection Against Adoptive Transfer of Autoimmune Diabetes Mediated Through Very Late Antigen–4 Integrin" *Diabetes* 43:529–534.

Yang et al. (1993) "Inhibition of Insulitis and Prevention of Diabetes in Nonobese Diabetic Mice by Blocking L–Selectin and Very Late Antigen 4 Adhesion Receptors" *Proc. Natl. Acad. Sci USA* 90:10494–10498.

Hammer et al. (1990) "Spontaneous Inflammatory Disease in Transgenic Rates Expressing HLA–B27 and Human $\beta_2$m: An Animal Model of HLA–B27–Associated Human Disorders" *Cell* 63:1099–1112.

Podolsky et al. (1993) "Attenuation of Colitis in the Cotton–top Tamarin by Anti–α4 Integrin Monoclonal Antibody" *J. Clin. Invest.* 92:372–380.

Strober et al. (1993) "Chronic Intestinal Inflammation: An Unexpected Outcome in Cytokine or T Cell Receptor Mutant Mice" *Cell* 75:203–205.

Turner et al. (1994) "Poxvirus Serpins" Chapter 6, in *Viroceptors, Virokines and Related Immune Modulators Encoded by DNA Viruses* G. McFadden, ed., R.G. Landes Company, Georgetown, Texas, 67–88.

McFadden et al. (1994) "Rabbit, Hare, Squirrel and Swine Poxviruses" in *Encyclopedia of Virology*, Poxviruses, Webster et al., eds. Academic Press, San Diego, 1153–1159.

McFadden et al. (1994) "Modulation of Cytokine Networks by Poxvirus: the Myxoma Virus Model" *Virology*, 5:421–429.

McFadden, "DNA Viruses That Affect Cytokine Networks" in *Human Cytokines: Their Role in Disease and Therapy:* Aggarwal et al., eds., Blackwell Scientific Cambridge, Mass., 401–420.

Macen et al. (1993) "SERP1, A Serine Proteinase Inhibitor Encoded by Myxoma Virus, Is a Secreted Glycoprotein That Interferes with Inflammation" *Virology* 195:348–363.

Liu et al. (1993) "A Novel Viral Anti–Infammatory Protein, SERP–1, Reduces Intimal Hyperplasia in Chloresterol–Fed Rabbits After Balloon Angioplasty" *Circulation* 88 (4 part 2):I81 (Abstract 0420).

Maksymowych et al. (1995) "Amelioration of Established Antigen–Induced Arthritis in Rabbits Treated with a Secreted Viral Serine Proteinase Inhibitor" *J. Rheumatol.* 22 (8): 1605 (Abstract).

McFadden et al. (1995) "Interruption of Cytokine Networks by Poxviruses: Lessons from Myxoma Virus" *J. Leukocyte Biology:57:* 731–738.

Stadius et al. (1993) "Local Infusion Balloon Angioplasty to Obviate Restenosis Compared with Conventional Balloon Angioplasty in an Experimental Model of Atherosclerosis" *Am. Heart J. 126* (1):47–56.

Wolinsky et al. (1990) "Use of a Perforated Balloon Catheter to Deliver Concentrated Heparin Into the Wall of the Normal Canine Artery" *JACC 15* (2):475–481.

Santoian et al. (1993) "Use of the Porous Balloon in Porcine Coronary Arteries: Rationale for Low Pressure and Volume Delivery" *Catheterization and Cardiovascular Diagnosis 30:* 348–354.

Gown et al. (1986) "Human Atherosclerosis– Immunocytochemical Analysis of the Cellular Composition of Human Atherosclerotic Lesions" *AJP 125* (1):191–207.

Fava et al. (1991) "Transforming Growth Factor β1 (TGF–β1) Induced Neutrophil Recruitment to Synovial Tissues: Implications for TGF–β–driven Synovial Inflammation and Hyperplasia" *J. Exp. Med. 173:*1121–1132.

Witkowski et al. (1993) "In Vivo Estimation of Cardiac Transmembrane Current" *Circulation Research 72* (2):424–439.

Ramaswamy et al. (1991) "Pathology of Pulmonary Parasitic Migration: Morphological and Bronchoalveolar Cellular Responses Following Nippostrongylus Brasiliensis Infection in Rats" *J. Parasitol. 77* (2):302–312.

Mathison et al. (1992) "Platelet Activating Factor and Systemic Anaphylasix in Nippostrongylus Brasiliensis–Sensitized Rats: Differential Effects of PAF Antagonists" *Br. J. Pharmacol. 106:*263–266.

Abraham et al. (1993) "Characterization of a Late Phase Pulmonary Response After Antigen Challenge in Allergic Sheep" *Am. Rev. Respir. Dis.128:*839–844.

Stokes et al. (1992) "An Electro–mechanical Spinal Injury Technique with Dynamic Sensitivity" *J. of Neutrotrauma 9* (3):187–195.

Popovich et al. (1994) "Elevation of the Neurotoxin Quinolinic Acid Occurs Following Spinal Cord Trauma" *Brain Research 633:*348–352.

Keelan et al. (1986) "Effect of External Abdominal Irradiation on Intestinal Morphology and Brush Border Membrane Enzyme and Lipid Composition" *Radiation Res. 105:*84–96.

Percy et al. (1993) "In Vitro Changes in the Properties of Rabbit Colonic Muscularis Mucosae in Colitis" *Gastroenterology 104:*369–376.

LeDuc et al. (1990) "Chemotactic Peptide–Induced Acute Colitis in Rabbits" *Gastroenterology 98:* 929–935.

Paul et al. (1992) "Macrophage Subpopulations in Normal and Transplanted Heart and Kidney Tissues in the Rat" *Transplant. 53* (1):157–162.

Zhang et al. (1994) "Characterization of a Murine Model of Myocarditis Induced by a Reactivated Coxsackievirus B3" *Int.J. Exp. Path. 75:*99–110.

Ben–Nun et al. (1981) "The Rapid Isolation of Clonable Antigen–Specific T Lymphocyte Lines Capable of Mediating Autoimmune Encephalomyelitis" *Eur. J. Immunol. 11:*195–199.

Hickey et al. (1991) "T–Lymphocyte Entry Into the Central Nervous System" *J. Neuroscience Res. 28:*254–260.

Howie et al. (1968) "The Immunology and Pathology of NZB Mice" *Adv. Immunol 198* (9): 215–266.

Theofilopoulos et al. (1985) "Murine Models of Systemic Lupus Erythematosus" *Advances in Immunol. 37:*269–390.

Doerschuk et al. (1990) "CD18–Dependent and –Independent Mechanisms of Neutrophil Emigration in the Pulmonary and Systemic Microcirculation of Rabbits" *J. of Immunol. 144* (6):2327–2333.

Kelly et al. (1994) "Antibody to Intercellular Adhesion Molecule 1 Protects the Kidney Against Ischemic Injury" *Proc. Natl. Acad. Sci. USA 91:* 812–816.

Okuda et al. (1990) "Elevated Expression of Transforming Growth Factor–β and Proteoglycan Production in Experimental Glomerulonephritis" *J. Clin. Invest. 86:*453–462.

Thomas et al. (1992) "Role of Leukocyte CD11/CD18 Complex in Endotoxic and Septic Shock in Rabbits" *J. Appl. Physiol. 73* (4):1510–1516.

Barsoum (1990) "Introduction of Stable High–Copy–Number DNA into Chinese Hamster Ovary Cells by Electroporation" *DNA and Cell Biol. 9* (4): 293–300.

Davision et al. (1990) "New Vaccinia Virus Recombination Plasmids Incroporating a Synthetic Late Promoter for High Level Expression of Foreign Proteins" *Nucl. Acids Res. 18* (14): 4285–4286.

Hagerty et al. (1993) "Tolerance to Self and the Processing and Presentation of Self Antigens" *Intern. Rev. Immunol. 10* (4):313–319.

Herzum et al. (1994) "Coxsackievirus B3 Infection Leads to Cell Death of Cardiac Myocytes" *J. Mol. Cell. Cardiol. 26* (7):907–913.

Huber et al. (1994) "Differential $Th_1$ and $Th_2$ Cell Responses in Male and Female BALB/c Mice Infected with Coxsackievirus Group B Type 3" *J. of Virology 68* (8):5126–5132.

Kasahara et al. (1994) "Autoimmune Myocarditis Induced in Mice by Cardiac C–Protein—Cloning of Complementary DNA Encloding Murine Cardiac C–Protein and Partial Characterization of the Antigenic Peptides" *J. Clin. Invest. 94* (3): 1026–1036.

Kavanagh et al. (1992) "High–Current Stimuli to the Spared Epicardium of a Large Infarct Induce Ventricular Tachycardia" *Circulation 85* (2):680–698.

Klinkert et al. (1985) "Surface Proteins of Mycoplasma Hyopneumoniae Identified From an *Escherichia Coli* Expression Plasmid Library" *Infection and Immunity 49* (2):329–335.

Kodama et al. (1994) "Rat Dilated Cardio–myopathy After Autoimmune Giant Cell Myocarditis" *Circulation Research 75* (2):278–284.

Kung et al. (1994) "Characterization of a Murine Model of Allergic Pulmonary Inflammation" *Int. Arch. Allergy. Immunol. 105* (1):83–90.

Miller et al. (1993) "Specific Interaction of Lymphocyte Function–associated Antigen 3 with CD2 Can Inhibit T Cell Responses" *J.Exp. Med. 178:*211–222.

Popovich et al. (1993) "Differential Expression of MHC Class II Antigen in the Contused Rat Spinal Cord" *J. Neurotrauma 10* (1):37–46.

Rabb et al. (1994) "The Role of the Leukocyte Adhesion Molecules VLA–4, LFA–1, and Mac–1 in Allergic Airway Responses in the Rat" *Am. J. Respir. Crit. Care Med. 149* (5):1186–1191.

Remaut et al. (1981) "Plasmid Vectors for High–Efficiency Expression Controlled by the $p_L$ Promoter of Coliphage Lambda" *Gene 15:*81–93.

Santing et al. (1994) "Dissociation Between Bronchial Hyperreactivity In Vivo and Reduced β–Adrenoceptor Sensitivity In Vitro in Allergen–Challenged Guinea Pigs" *Eur. J. Pharm. 257:*145–152.

Tanaka et al. (1994) "An Angiotensin II Receptor Antagonist Reduces Myocardial Damage in an Animal Model of Myocarditis" *Circulation 90* (4): 2051–2055.

Yanos et al. (1994) "Mechanism of Respiratory Arrest in an Animal Model of Acute Fatal Bronchoconstriction" *J. Appl. Physiol. 77* (1): 236–244.

```
ATGAAGTATCTGGTCCTCGTCTTATGTTTAACGTCGTGCGCGTGTCGAGATATCGGAC    58
 M  R  Y  L  V  L  V  L  C  L  T  S  C  A  C  R  D  I  G  L   20

TATGGACGTTCCGATACGTCTACAACGAAAGCGACAACGTCGTGTTCTCACCGTACGGCT  118
 W  T  F  R  Y  V  Y  N  E  S  D  N  V  V  F  S  P  Y  G  L   40

TGACCTCCGCGTTGTCCGTGTTACGGATCGCGGCGGGCGGTAACACGAAACGAGAAATAG  178
 T  S  A  L  S  V  L  R  I  A  A  G  G  N  T  K  R  E  I  D   60

ACGTCCCCGAATCCGTCGTGGAGGACTCCGACGCCTTTCTCGCGTTACGGGAGTTGTTCG  238
 V  P  E  S  V  V  E  D  S  D  A  F  L  A  L  R  E  L  F  V   80

TAGACGCATCCGTTCCGTTACGTCCCGAGTTTACGGCGGAGTTCTCCTCGCGATTCAATA  298
 D  A  S  V  P  L  R  P  E  F  T  A  E  F  S  S  R  F  N  T  100

CCTCCGTGCAACGCGTGACGTTTAACTCGGAGAACGTCAAAGACGTCATTAACTCGTACG  348
 S  V  Q  R  V  T  F  N  S  E  N  V  K  D  V  I  N  S  Y  V  120

TTAAGGATAAGACGGGAGGAGACGTCCCACGCGTATTGGACGCCTCCCTAGACCGAGATA  408
 K  D  K  T  G  G  D  V  P  R  V  L  D  A  S  L  D  R  D  T  140

CTAAAATGCTGCTATTGAGCTCCGTTCGTATGAAGACGAGCTGGAGACACGTATTCGACC  468
 K  M  L  L  L  S  S  V  R  M  K  T  S  W  R  H  V  F  D  P  160

CTTCGTTCACGACGGATCAACCTTTTTATTCCGGAAACGTCACATACAAGGTACGTATGA  528
 S  F  T  T  D  Q  P  F  Y  S  G  N  V  T  Y  K  V  R  M  M  180

TGAATAAAATAGATACGTTGAAAACGGAGACGTTTACGCTTAGAAACGTGGGATACTCCG  588
 N  K  I  D  T  L  K  T  E  T  F  T  L  R  N  V  G  Y  S  V  200

TAACGGAACTGCCGTATAAACGGCGTCAAACGGCCATGTTGCTCGTCGTTCCGGACGACT  648
 T  E  L  P  Y  K  R  R  Q  T  A  M  L  L  V  V  P  D  D  L  220

TGGGAGAGATCGTGCGGGCCCTCGATCTTTCTCTAGTACGCTTCTGGATACGCAACATGA  708
 G  E  I  V  R  A  L  D  L  S  L  V  R  F  W  I  R  N  M  R  240

GGAAAGACGTGTGTCAGGTGGTAATGCCCAAGTTCTCCGTCGAATCGGTCCTGGATCTGA  768
 K  D  V  C  Q  V  V  M  P  K  F  S  V  E  S  V  L  D  L  R  260

GGGACGCCCTCCAGAGACTGGGGGTGCGAGACGCGTTCGATCCATCCCGGGCGGACTTCG  828
 D  A  L  Q  R  L  G  V  R  D  A  F  D  P  S  R  A  D  F  G  280

GTCAGGCGTCCCCGTCGAACGATCTATACGTCACGAAGGTGTTACAGACGTCCAAGATAG  888
 Q  A  S  P  S  N  D  L  Y  V  T  K  V  L  Q  T  S  K  I  E  300

AGGCGGACGAACGGGGAACGACGGCGTCGAGCGACACAGCCATCACCCTCATCCCCAGGA  948
 A  D  E  R  G  T  T  A  S  S  D  T  A  I  T  L  I  P  R  N  320

ACGCCCTCACGGCGATCGTGGCGAACAAACCGTTTATGTTTCTCATCTATCACAAGCCTA 1008
 A  L  T  A  I  V  A  N  K  P  F  M  F  L  I  Y  H  K  P  T  340

CAACGACCGTGTTGTTTATGGGAACGATAACAAAGGGTGAAAAAGTAATATACGATACGG 1068
 T  T  V  L  F  M  G  T  I  T  K  G  E  K  V  I  Y  D  T  E  360

AGGGTCGAGATGATGTCGTATCCTCTGTATAAACTCTTTTTGAAGGGTAAACTATGCGAC 1128
 G  R  D  D  V  V  S  S  V  *                                 369
```

FIG.1

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1138 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1107

(xi) SEQUENCE DESCRIPTION: SEQ ID NO:1:

```
ATG AAG TAT CTG GTC CTC GTC TTA TGT TTA ACG TCG TGC GCG TGT CGA      48
Met Lys Tyr Leu Val Leu Val Leu Cys Leu Thr Ser Cys Ala Cys Arg
 1               5                  10                  15

GAT ATC GGA CTA TGG ACG TTC CGA TAC GTC TAC AAC GAA AGC GAC AAC      96
Asp Ile Gly Leu Trp Thr Phe Arg Tyr Val Tyr Asn Glu Ser Asp Asn
            20                  25                  30

GTC GTG TTC TCA CCG TAC GGC TTG ACC TCC GCG TTG TCC GTG TTA CGG     144
```

```
Val Val Phe Ser Pro Tyr Gly Leu Thr Ser Ala Leu Ser Val Leu Arg
         35                  40                  45

ATC GCG GCG GGC GGT AAC ACG AAA CGA GAA ATA GAC GTC CCC GAA TCC         192
Ile Ala Ala Gly Gly Asn Thr Lys Arg Glu Ile Asp Val Pro Glu Ser
50                  55                  60

GTC GTG GAG GAC TCC GAC GCC TTT CTC GCG TTA CGG GAG TTG TTC GTA         240
Val Val Glu Asp Ser Asp Ala Phe Leu Ala Leu Arg Glu Leu Phe Val
65                  70                  75                  80

GAC GCA TCC GTT CCG TTA CGT CCC GAG TTT ACG GCG GAG TTC TCC TCG         288
Asp Ala Ser Val Pro Leu Arg Pro Glu Phe Thr Ala Glu Phe Ser Ser
                85                  90                  95

CGA TTC AAT ACC TCC GTG CAA CGC GTG ACG TTT AAC TCG GAG AAC GTC         336
Arg Phe Asn Thr Ser Val Gln Arg Val Thr Phe Asn Ser Glu Asn Val
            100                 105                 110

AAA GAC GTC ATT AAC TCG TAC GTT AAG GAT AAG ACG GGA GGA GAC GTC         384
Lys Asp Val Ile Asn Ser Tyr Val Lys Asp Lys Thr Gly Gly Asp Val
            115                 120                 125

CCA CGC GTA TTG GAC GCC TCC CTA GAC CGA GAT ACT AAA ATG CTG CTA         432
Pro Arg Val Leu Asp Ala Ser Leu Asp Arg Asp Thr Lys Met Leu Leu
130                 135                 140

TTG AGC TCC GTT CGT ATG AAG ACG AGC TGG AGA CAC GTA TTC GAC CCT         480
Leu Ser Ser Val Arg Met Lys Thr Ser Trp Arg His Val Phe Asp Pro
145                 150                 155                 160

TCG TTC ACG ACG GAT CAA CCT TTT TAT TCC GGA AAC GTC ACA TAC AAG         528
Ser Phe Thr Thr Asp Gln Pro Phe Tyr Ser Gly Asn Val Thr Tyr Lys
                165                 170                 175

GTA CGT ATG ATG AAT AAA ATA GAT ACG TTG AAA ACG GAG ACG TTT ACG         576
Val Arg Met Met Asn Lys Ile Asp Thr Leu Lys Thr Glu Thr Phe Thr
            180                 185                 190

CTT AGA AAC GTG GGA TAC TCC GTA ACG GAA CTG CCG TAT AAA CGG CGT         624
Leu Arg Asn Val Gly Tyr Ser Val Thr Glu Leu Pro Tyr Lys Arg Arg
            195                 200                 205

CAA ACG GCC ATG TTG CTC GTC GTT CCG GAC GAC TTG GGA GAG ATC GTG         672
Gln Thr Ala Met Leu Leu Val Val Pro Asp Asp Leu Gly Glu Ile Val
210                 215                 220

CGG GCC CTC GAT CTT TCT CTA GTA CGC TTC TGG ATA CGC AAC ATG AGG         720
Arg Ala Leu Asp Leu Ser Leu Val Arg Phe Trp Ile Arg Asn Met Arg
225                 230                 235                 240

AAA GAC GTG TGT CAG GTG GTA ATG CCC AAG TTC TCC GTC GAA TCG GTC         768
Lys Asp Val Cys Gln Val Val Met Pro Lys Phe Ser Val Glu Ser Val
                245                 250                 255

CTG GAT CTG AGG GAC GCC CTC CAG AGA CTG GGG GTG CGA GAC GCG TTC         816
Leu Asp Leu Arg Asp Ala Leu Gln Arg Leu Gly Val Arg Asp Ala Phe
            260                 265                 270

GAT CCA TCC CGG GCG GAC TTC GGT CAG GCG TCC CCG TCG AAC GAT CTA         864
Asp Pro Ser Arg Ala Asp Phe Gly Gln Ala Ser Pro Ser Asn Asp Leu
            275                 280                 285

TAC GTC ACG AAG GTG TTA CAG ACG TCC AAG ATA GAG GCG GAC GAA CGG         912
Tyr Val Thr Lys Val Leu Gln Thr Ser Lys Ile Glu Ala Asp Glu Arg
290                 295                 300

GGA ACG ACG GCG TCG AGC GAC ACA GCC ATC ACC CTC ATC CCC AGG AAC         960
Gly Thr Thr Ala Ser Ser Asp Thr Ala Ile Thr Leu Ile Pro Arg Asn
305                 310                 315                 320

GCC CTC ACG GCG ATC GTG GCG AAC AAA CCG TTT ATG TTT CTC ATC TAT        1008
Ala Leu Thr Ala Ile Val Ala Asn Lys Pro Phe Met Phe Leu Ile Tyr
                325                 330                 335

CAC AAG CCT ACA ACG ACC GTG TTG TTT ATG GGA ACG ATA ACA AAG GGT        1056
His Lys Pro Thr Thr Thr Val Leu Phe Met Gly Thr Ile Thr Lys Gly
            340                 345                 350

GAA AAA GTA ATA TAC GAT ACG GAG GGT CGA GAT GAT GTC GTA TCC TCT        1104
```

-continued

```
Glu Lys Val Ile Tyr Asp Thr Glu Gly Arg Asp Asp Val Val Ser Ser
        355                 360                 365

GTA TAAACTCTTT TTGAAGGGTA AACTATGCGA C                              1138
Val
```

(2) INFORMATION FOR SEQ ID NO:2:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Tyr Leu Val Leu Val Leu Cys Leu Thr Ser Cys Ala Cys Arg
 1               5                  10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95

Arg Phe Asn Thr Ser Val Gln Arg Val Thr Phe Asn Ser Glu Asn Val
            100                 105                 110

Lys Asp Val Ile Asn Ser Tyr Val Lys Asp Lys Thr Gly Gly Asp Val
        115                 120                 125

Pro Arg Val Leu Asp Ala Ser Leu Asp Arg Asp Thr Lys Met Leu Leu
    130                 135                 140

Leu Ser Ser Val Arg Met Lys Thr Ser Trp Arg His Val Phe Asp Pro
145                 150                 155                 160

Ser Phe Thr Thr Asp Gln Pro Phe Tyr Ser Gly Asn Val Thr Tyr Lys
                165                 170                 175

Val Arg Met Met Asn Lys Ile Asp Thr Leu Lys Thr Glu Thr Phe Thr
            180                 185                 190

Leu Arg Asn Val Gly Tyr Ser Val Thr Glu Leu Pro Tyr Lys Arg Arg
        195                 200                 205

Gln Thr Ala Met Leu Leu Val Val Pro Asp Asp Leu Gly Glu Ile Val
    210                 215                 220

Arg Ala Leu Asp Leu Ser Leu Val Arg Phe Trp Ile Arg Asn Met Arg
225                 230                 235                 240

Lys Asp Val Cys Gln Val Val Met Pro Lys Phe Ser Val Glu Ser Val
                245                 250                 255

Leu Asp Leu Arg Asp Ala Leu Gln Arg Leu Gly Val Arg Asp Ala Phe
            260                 265                 270

Asp Pro Ser Arg Ala Asp Phe Gly Gln Ala Ser Pro Ser Asn Asp Leu
        275                 280                 285

Tyr Val Thr Lys Val Leu Gln Thr Ser Lys Ile Glu Ala Asp Glu Arg
    290                 295                 300

Gly Thr Thr Ala Ser Ser Asp Thr Ala Ile Thr Leu Ile Pro Arg Asn
305                 310                 315                 320

Ala Leu Thr Ala Ile Val Ala Asn Lys Pro Phe Met Phe Leu Ile Tyr
                325                 330                 335
```

—continued

```
His Lys Pro Thr Thr Thr Val Leu Phe Met Gly Thr Ile Thr Lys Gly
            340                 345                 350

Glu Lys Val Ile Tyr Asp Thr Glu Gly Arg Asp Asp Val Val Ser Ser
            355                 360                 365

Val
```

METHODS OF TREATING INFLAMMATION AND COMPOSITIONS THEREFOR

BACKGROUND OF THE INVENTION

The present invention relates to use of a viral protein, SERP-1, its analogs and biologically active fragments thereof in the prevention and treatment of inflammatory and immune reactions associated with numerous injuries and disease conditions.

Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter referred to as cellular infiltration). Roitt et al., *Immunology*, Grower Medical Publishing, New York, 1989.

Increased capillary permeability allows larger molecules to cross the endothelium that are not ordinarily capable of doing so, thereby allowing soluble mediators of immunity such as leukocytes to reach the injured or infected site. Leukocytes, primarily neutrophil polymorphs (also known as polymorphonuclear leukocytes, neutrophils or PMNS) and macrophages, migrate to the injured site by a process known as chemotaxis. At the site of inflammation, tissue damage and complement activation cause the release of chemotactic peptides such as C5a. Id. Complement activation products are also responsible for causing degranulation of phagocytic cells, mast cells and basophils, smooth muscle contraction and increases in vascular permeability. Mulligan et al. 1991 *J. Immunol.* 148:1479–1485.

The traversing of leukocytes from the bloodstream to extravascular sites of inflammation or immune reaction involves a complex but coordinated series of events. At the extravascular site of infection or tissue injury, signals are generated such as bacterial endotoxins, activated complement fragments or proinflammatory cytokines such as interleukin 1 (IL-1), interleukin 6 (IL-6), and tumor necrosis factor (TNF) which activate leukocytes and/or endothelial cells and cause one or both of these cell types to become adhesive. Initially, cells become transiently adhesive (manifested by rolling) and later, such cells become firmly adhesive (manifested by sticking). Adherent leukocytes travel across the endothelial cell surface, diapedese between endothelial cells and migrate through the subendothelial matrix to the site of inflammation or immune reaction. Harlan et al., *Adhesion-Its role in Inflammatory Disease*, W. H. Freeman & Co., New York, 1992.

Although leukocyte traversal of vessel walls to extravascular tissue is necessary for host defense against foreign antigens and organisms, leukocyte-endothelial interactions often have deleterious consequences for the host. For example, during the process of adherence and transendothelial migration, leukocytes release oxidants, proteases and cytokines that directly damage endothelium or cause endothelial dysfunction. Once at the extravascular site, emigrated leukocytes further contribute to tissue damage by releasing a variety of inflammatory mediators. Moreover, single leukocytes sticking within the capillary lumen or aggregation of leukocytes within larger vessels are responsible for microvascular occlusion and ischemia. Leukocyte-mediated vascular and tissue injury has been implicated in pathogenesis of a wide variety of clinical disorders such as acute and chronic allograft rejection, vasculitis, rheumatoid and other forms of inflammatory based arthritis, inflammatory skin diseases, adult respiratory distress syndrome, ischemia-reperfusion syndromes such as myocardial infarction, shock, stroke, organ transplantation, crush injury and limb replantation. Id.

Many other serious clinical conditions involve underlying inflammatory processes in humans. For example, multiple sclerosis (MS) is an inflammatory disease of the central nervous system. In MS, circulating leukocytes infiltrate inflamed brain endothelium and damage myelin, with resultant impaired nerve conduction and paralysis. Yednock et al., 1992 *Nature* 366:63–66. Systemic lupus erythematosus (SLE) is an autoimmune disease characterized by the presence of tissue damage caused by self antigen directed antibodies. Auto-antibodies bound to antigens in various organs lead to complement-mediated and inflammatory cell mediated tissue damage. Theofilopoubs, A.N. 1992 *Encyclopedia of Immunology*, pp. 1414–1417.

Reperfusion injury is another condition associated with activation of the inflammatory system and enhanced leukocyte-endothelial cell (EC) adhesion. There is much evidence that adhesion-promoting molecules facilitate interactions between leukocytes and endothelial cells and play important roles in acute inflammatory reaction and accompanying tissue injury. For example, in acute lung injury caused by deposition of IgG immune complexes or after bolus i.v. infusion of cobra venom factor (CVF), neutrophil activation and the generation of toxic oxygen metabolites cause acute injury. Mulligan et al., 1992 *J. Immunol.* 150 (6):2401–2405. Neutrophils (PMNs) are also known to mediate ischemia/reperfusion injury in skeletal and cardiac muscle, kidney and other tissues. Pemberton et al., 1993 *J. Immunol.* 150:5104–5113.

Infiltration of airways by inflammatory cells, particularly eosinophils, neutrophils and T lymphocytes are characteristic features of atopic or allergic asthma. Cotran et al., *Pathological Basis of Disease*, W. B. Saunders, Philadelphia, 1994. Cellular infiltration of the pancreas with resultant destruction of islet beta-cells is the underlying pathogenesis associated with insulin-dependent diabetes melitis. Burkly et al. 1994 *Diabetes* 43: 529–534. Activation of inflammatory cells whose products cause tissue injury underlies the pathology of inflammatory bowel diseases such as Crohn's disease and ulcerative colitis. Cotran et al., 1994. Neutrophils, eosinophils, mast cells, lymphocytes and macrophages contribute to the inflammatory response. Minute microabcesses of neutrophils in the upper epithelial layers of the dermis accompany the characteristic epidermal hyperplasia/thickening and scaling in psoriasis.

Various anti-inflammatory drugs are currently available for use in treating conditions involving underlying inflammatory processes. Their effectiveness however, is widely variable and there remains a significant clinical unmet need. This is especially true in the aforementioned diseases where available therapy is either of limited effectiveness or is accompanied by unwanted side effect profiles. Moreover, few clinical agents are available which directly inhibit cellular infiltration, a major underlying cause of tissue damage associated with inflammation. Thus, there is a need for a safe, effective clinical agent for preventing and ameliorating cellular infiltration and consequential pathologic conditions associated with inflammatory diseases, injuries and resultant perturbations of cytokine networks.

Serine proteinase inhibitors (hereinafter "serpins") make up a superfamily of related proteins and have been found encoded by poxviruses from four different genera. Myxoma virus (MYX) is a leporipoxvirus that causes a virulent systemic infection, myxomatosis, in the European rabbit (*Oryctolagus cuniculus*). Significantly, myxomatosis is characterized by rapid disseminated infection, immunosuppression, and the presence of secondary, gram negative infections. A closely related leporipoxvirus, Shope fibroma virus (SFV), causes only a localized infection in the same host. SFV differs from the virulent myxoma virus in that it contains only a fragmented open reading frame (ORF) for a corresponding myxoma virus ORF designated SERP-1. A disruption of the SERP-1 ORF in myxoma virus or in the related malignant rabbit fibroma virus (MRV) results in attenuation of virus pathogenicity in *O. cuniculus*. Macen et al., 1993 *Virology* 195:348–363. Thus, SERP-1 has been generally implicated in the complex response to leporipoxviral infection in its natural host, *O. cuniculus*. Although the absence of SERP-1 from myxoma virus apparently causes an increased immune response in rabbit, the mechanism by which SERP-1 acts as a virulence factor is unclear.

Recently, the SERP-1 polypeptide has been demonstrated to decrease intimal fatty cellular proliferation associated with restenosis in rabbits following balloon angioplasty. Lucas et al., 1994 *J. Cell. Biochem. Suppl.* 18A:286; Liu et al., 1993 *Circulation* 88:I-81.

It has been discovered in accordance with the present invention that SERP-1, SERP-1 analogs and biologically active fragments thereof are capable of directly inhibiting the infiltration of tissue by inflammatory cells that are responsible for tissue damage in inflammatory diseases and disorders.

SUMMARY OF THE INVENTION

In accordance with the present invention, it has been surprisingly discovered that the protein SERP-1, a serine protease inhibitor produced by malignant rabbit fibroma virus (MRV) and myxoma virus (MYX), its analogs and biologically active fragments thereof, prevent and reduce infiltration of inflammatory cells in injured and diseased tissues and in animals besides the rabbit for clinical manifestations that are of non-viral origin. The present invention therefore, is efficacious for preventing and reducing inflammatory cell infiltration in a diseased or injured tissue of a subject and the physiological symptoms associated therewith.

The present invention provides a method for treating diseases and injuries involving inflammatory and immune reactions. In accordance with the present invention, SERP-1, SERP-1 analogs or biologically active fragments thereof, are administered to a subject in need of such treatment for a time and under conditions sufficient to prevent, inhibit, and/or ameliorate the inflammatory or immune reactions.

One embodiment of the invention is directed to preventing, inhibiting and/or ameliorating inflammatory and immune reactions associated with conditions involving hyperactive airways such as asthma. Another embodiment of the invention is directed to preventing, inhibiting and/or ameliorating inflammatory and immune reactions associated with systemic lupus erythematosus. Another embodiment is directed to preventing, inhibiting and/or ameliorating inflammatory and immune reactions associated with multiple sclerosis. Yet another embodiment of the invention is directed to preventing, inhibiting and/or ameliorating inflammatory and immune reactions associated with inflammatory arthritis. In all of these embodiments of the invention, the SERP-1, SERP-1 analog or biologically active fragment thereof is delivered in a manner consistent with conventional methodologies associated with treatment of asthma, systemic lupus erythematosus, multiple sclerosis, and inflammatory arthritis such as for example, intravenously, intra-articularly, intraperitoneally, intra-arterialy, intramuscularly, intrarectally, subcutaneously, or by aerosol inhalant in order to inhibit or ameliorate inflammatory and immune reactions associated with such diseases.

Other embodiments of the invention are directed to preventing, inhibiting and/or ameliorating inflammatory and immune reactions associated with injuries and diseases such as: coronary arterial occlusion, cardiac arrhythmias, congestive heart failure, cardiomyopathy, bronchitis, acute allergic reactions and hypersensitivity, neurotrauma, inflammatory bowel diseases, psoriasis, systemic shock injury, graft/transplant rejection, myocarditis, insulin dependent diabetes, and stroke. In these embodiments of the invention, the SERP-1, SERP-1 analog or biologically active fragment is delivered in a manner consistent with conventional methodologies associated with treatment of the relevant injury or disease condition such as for example, intravenously, intra-articularly, intraarterially, intraperitoneally, subcutaneously, intramuscularly, intrarectally, topically or by aerosol inhalant in order to inhibit and ameliorate inflammatory and immune reactions associated with such diseases.

In another embodiment of the present invention, pharmaceutical compositions are provided which include SERP-1, its analogs or biologically active fragments thereof admixed with a pharmaceutically acceptable carrier.

In a further embodiment, the present invention is directed to an article of manufacture comprising packaging material and SERP-1, SERP-1 analog, or biologically active fragment thereof within the packaging material and wherein the pharmaceutical agent is effective for treating inflammatory conditions such as arthritis, inflammatory bowel disease, systemic lupus erythematosus, and multiple sclerosis and wherein the packaging material comprises a label which indicates that the pharmaceutical agent can be used for treating such inflammatory conditions.

These and other objects of the invention are accomplished by the administration of SERP-1, its analogs and biologically active fragments thereof in amounts sufficient to achieve the desired therapeutic effect.

BRIEF DESCRIPTION OF THE DRAWINGS

FIG. 1 depicts the nucleotide and corresponding amino acid sequence of the Myxoma virus (MYX) SERP-1 open reading frame (SEQ ID NO:1).

distribution at the primary site 24 hours after 30 ng SERP-1 infusion (magnification 260×).

Figure 2:
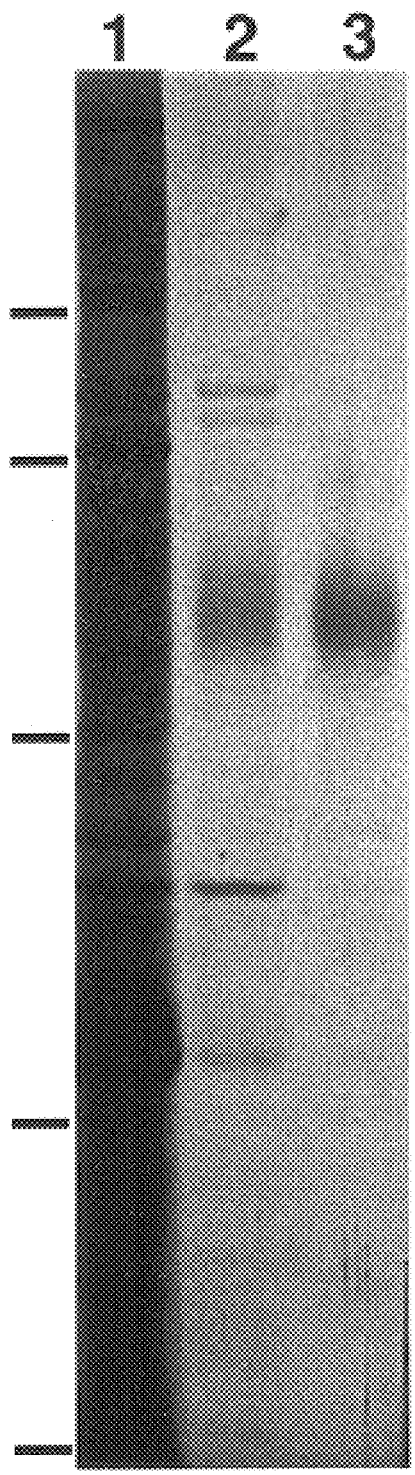
FIG. 2 is a photograph showing electrophoretic migration patterns of the mature, processed SERP-1 protein and vaccinia vector control in a silver stained SDS polyacrylamide gel. Lane 1 shows the electrophoretic pattern of Mono-Q purified VV-601 (control vector). Lane 2 shows the electrophoretic pattern of the Mono-Q purified SERP-1 protein secreted from baby Green monkey kidney (BGMK) cells infected with VV-S1. Lane 3 depicts the electrophoretic pattern of the SERP-1 further purified to homogeneity using Superdex 75.
Figure 3A:
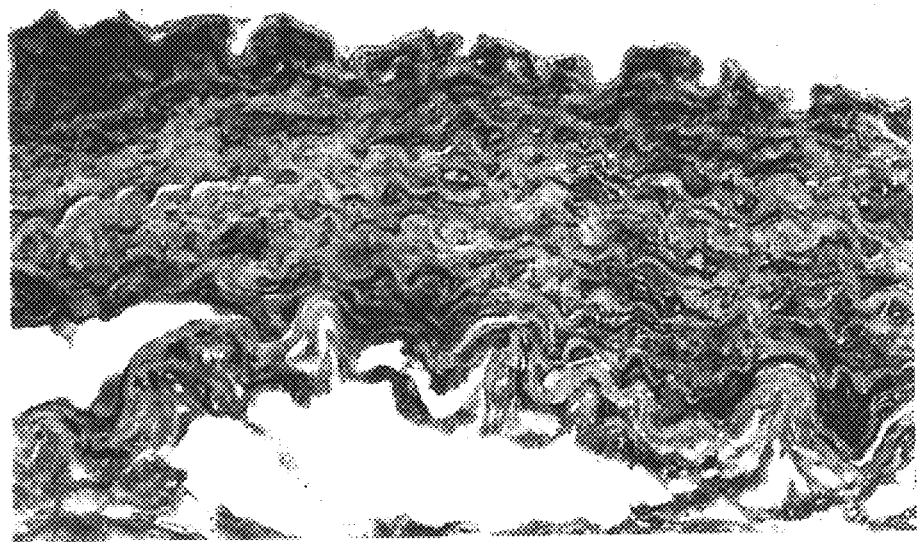
FIG. 3A shows an immunostained section of rabbit aorta with smooth muscle cell (alpha actin antibody) distribution at the primary site 24 hours after 3 ng SERP-1 infusion (Magnification 260×).
Figure 3B:
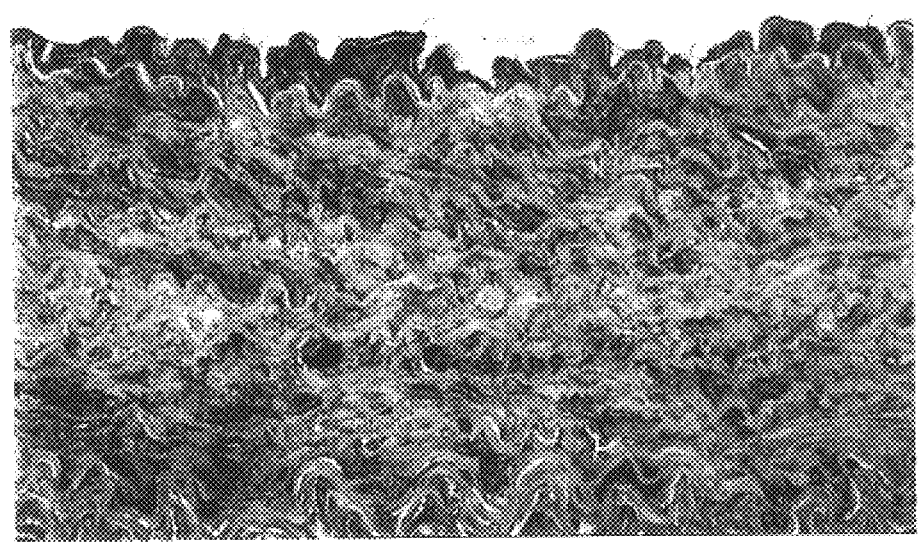
FIG. 3B shows an immunostained section of rabbit aorta with smooth muscle cell (alpha actin antibody) distribution at the primary site 24 hours after control saline infusion (magnification 260×).
Figure 3C:
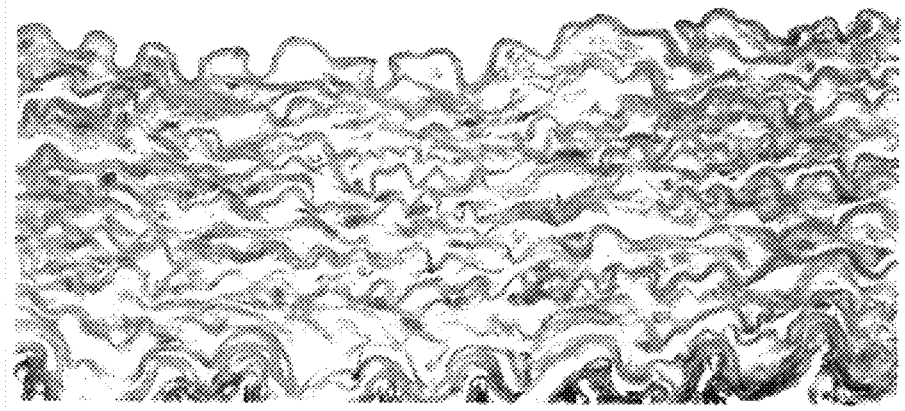
FIG. 3C shows an immunostained section of rabbit aorta with mononuclear leukocyte (CD11b antibody positive)
Figure 3D:
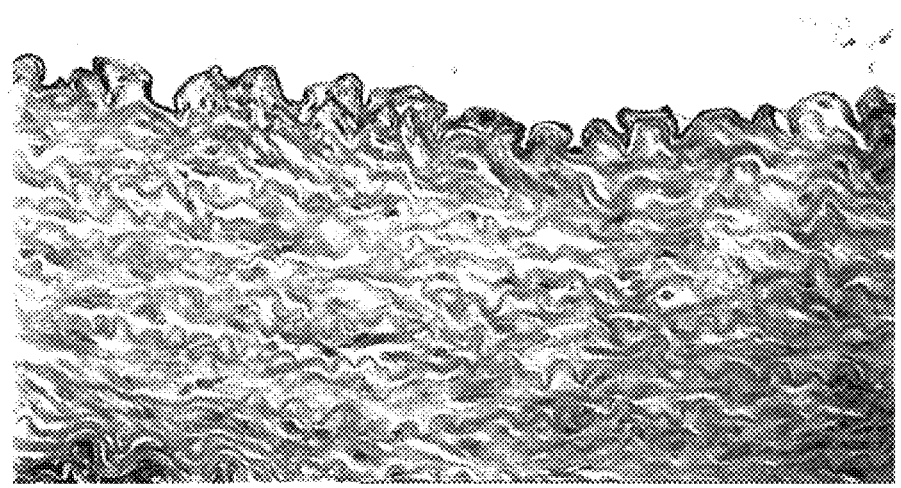

FIG. 3D shows an immunostained section of rabbit aorta with mononuclear leukocyte (CD11b antibody positive) distribution at the primary site 24 hours after control saline infusion (magnification 260×).

Figure 3E:
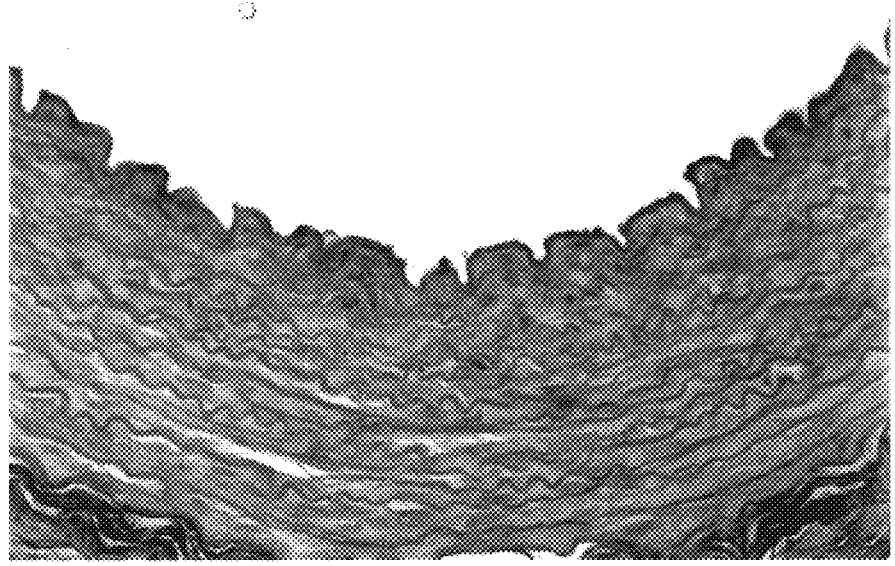

FIG. 3E shows an immunostained section of rabbit aorta with T lymphocyte (anti-CD25 positive) distribution at the primary site 24 hours after 30 ng SERP-1 infusion (magnification 400×).

Figure 3F:
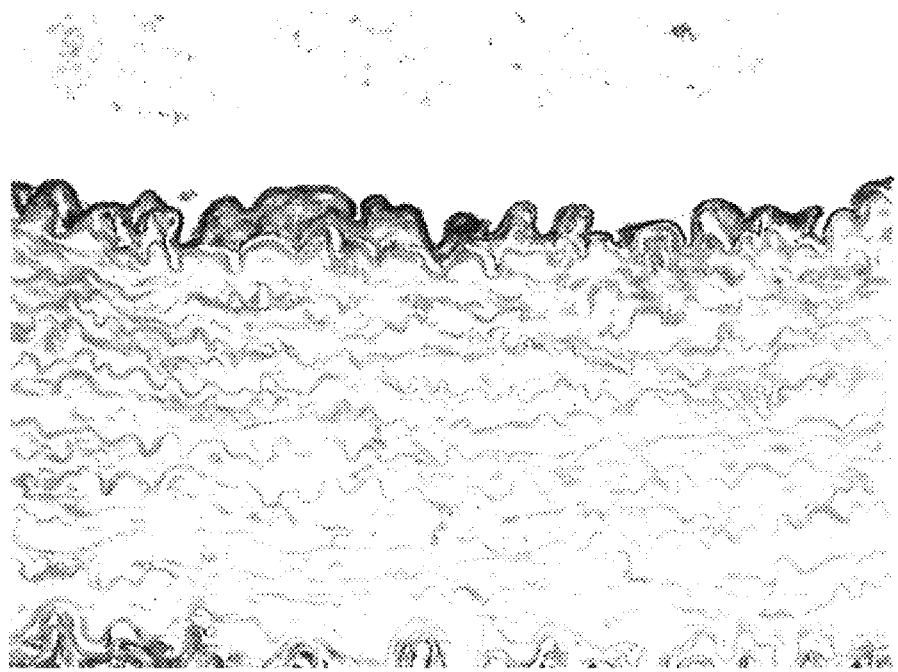

FIG. 3F shows an immunostained section of rabbit aorta with T lymphocyte (anti-CD25 positive) distribution at the primary site 24 hours after control saline infusion (magnification 400×).

Figure 3G:
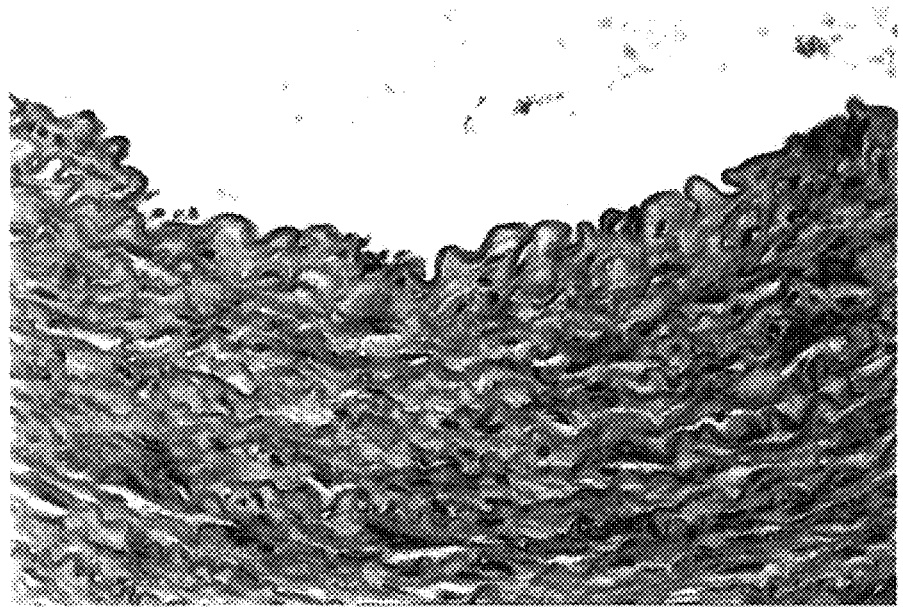

FIG. 3G shows an immunostained section of rabbit aorta with macrophage (RAM11 positive) distribution at a primary site 24 hours after 3 ng of SERP-1 infusion (magnification 400×).

Figure 3H:
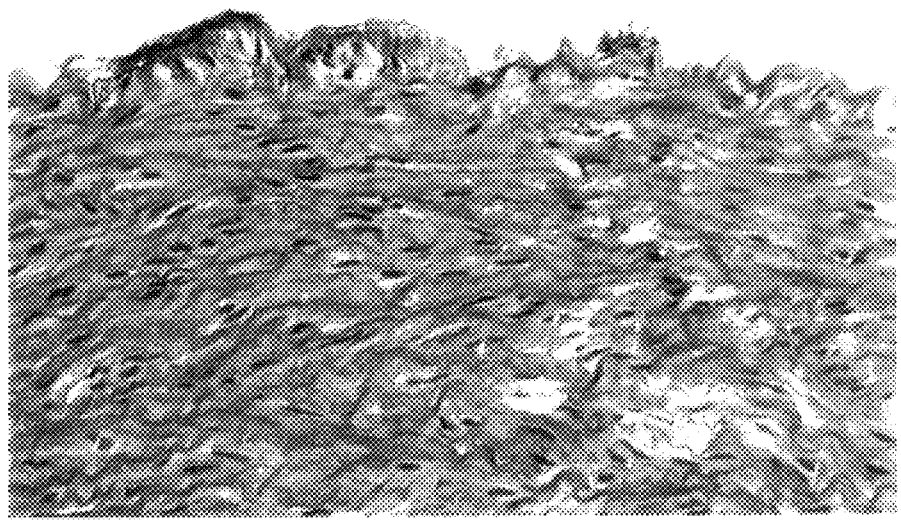

FIG. 3H shows an immunostained section of rabbit aorta with macrophage (RAM11 positive) distribution at a primary site 24 hours after saline infusion (magnification 400×).

Figure 4A:
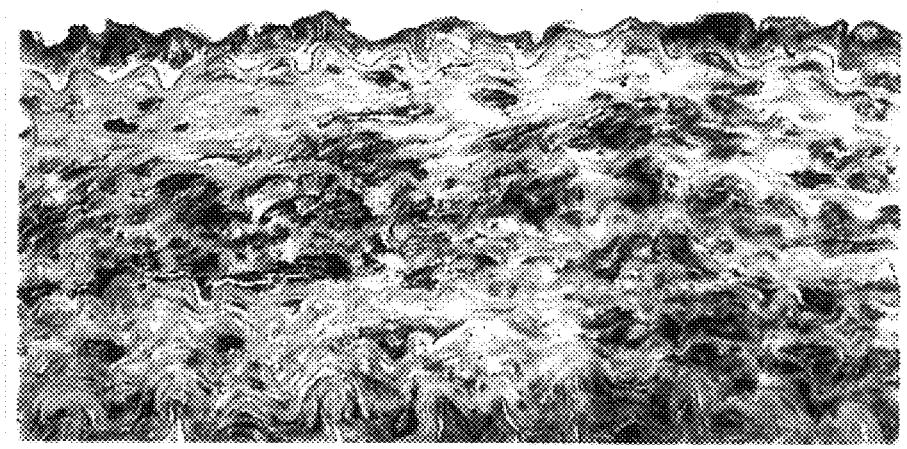

FIG. 4A shows an immunostained section of rabbit aorta with smooth muscle cell (alpha actin antibody) distribution at the primary site 4 weeks after 3 ng SERP-1 infusion (Magnification 400×).

Figure 4B:
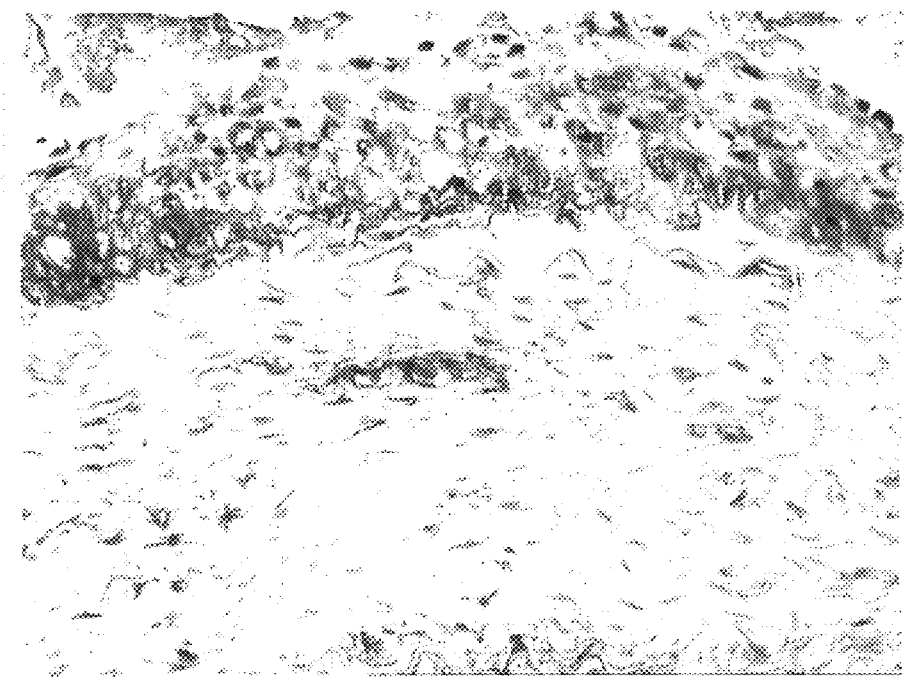

FIG. 4B shows an immunostained section of rabbit aorta with smooth muscle cell (alpha actin antibody) distribution at the primary site 4 weeks after control saline infusion (magnification 260×).

Figure 4C:
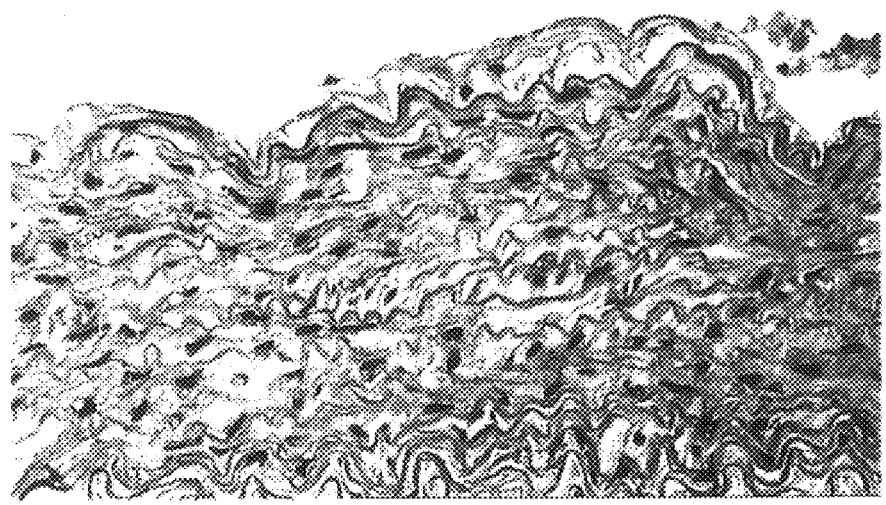

FIG. 4C shows an immunostained section of rabbit aorta with mononuclear leukocyte (CD11b antibody positive) distribution at the primary site 4 weeks after 30 ng SERP-1 infusion (magnification 260×).

Figure 4D:
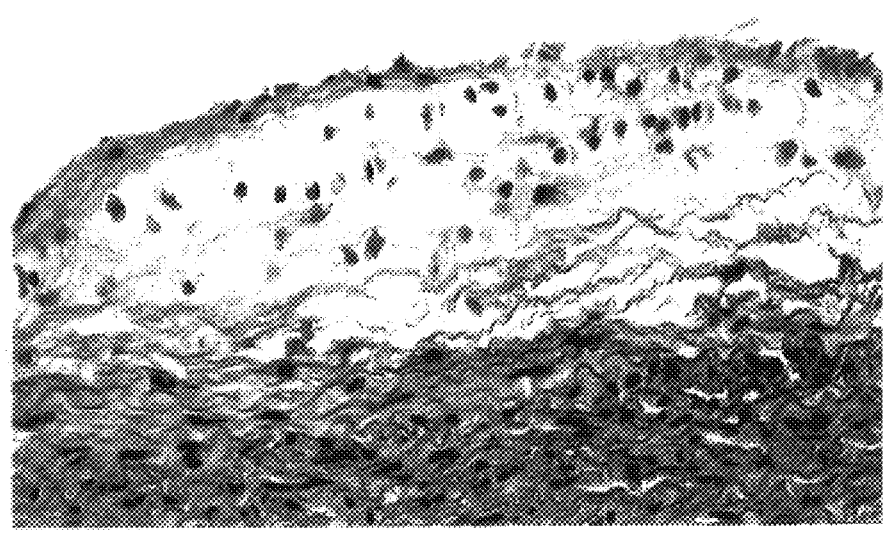

FIG. 4D shows an immunostained section of rabbit aorta with mononuclear leukocyte (CD11b antibody positive) distribution at the primary site 4 weeks after control saline infusion (magnification 260×).

Figure 4E:
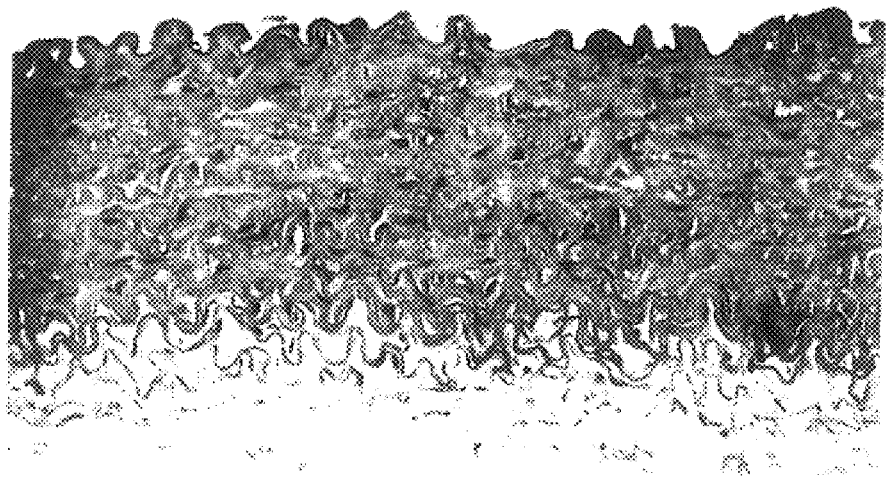

FIG. 4E shows an immunostained section of rabbit aorta with T lymphocyte (anti-CD25 positive) distribution at the primary site 4 weeks after 30 ng SERP-1 infusion (magnification 260×).

Figure 4F:
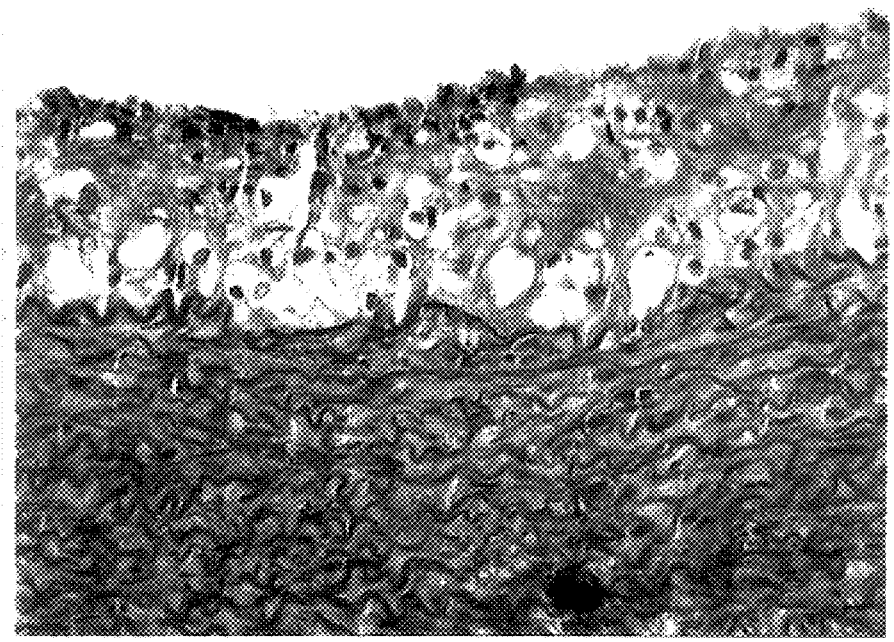

FIG. 4F shows an immunostained section of rabbit aorta with T lymphocyte (anti-CD25 positive) distribution at the primary site 4 weeks after control saline infusion (magnification 260×).

Figure 4G:
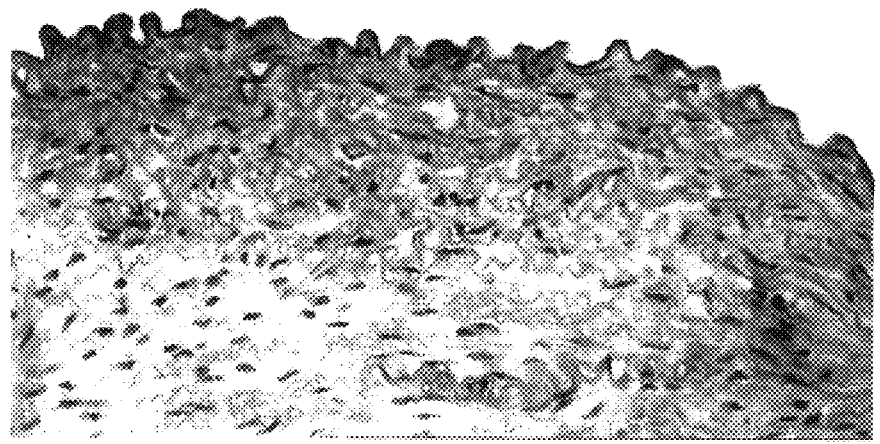

FIG. 4G shows an immunostained section of rabbit aorta with macrophage (RAM11 positive) distribution at a primary site 4 weeks after 3 ng of SERP-1 infusion (magnification 260×).

Figure 4H:
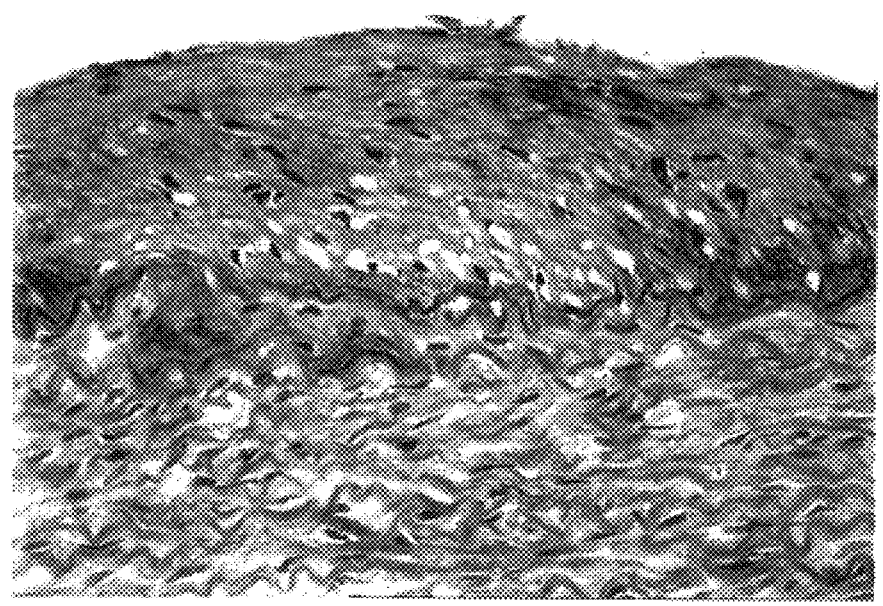

FIG. 4H shows an immunostained section of rabbit aorta with macrophage (RAM11 positive) distribution at a primary site 24 hours after saline infusion (magnification 260×).

Figure 5A:
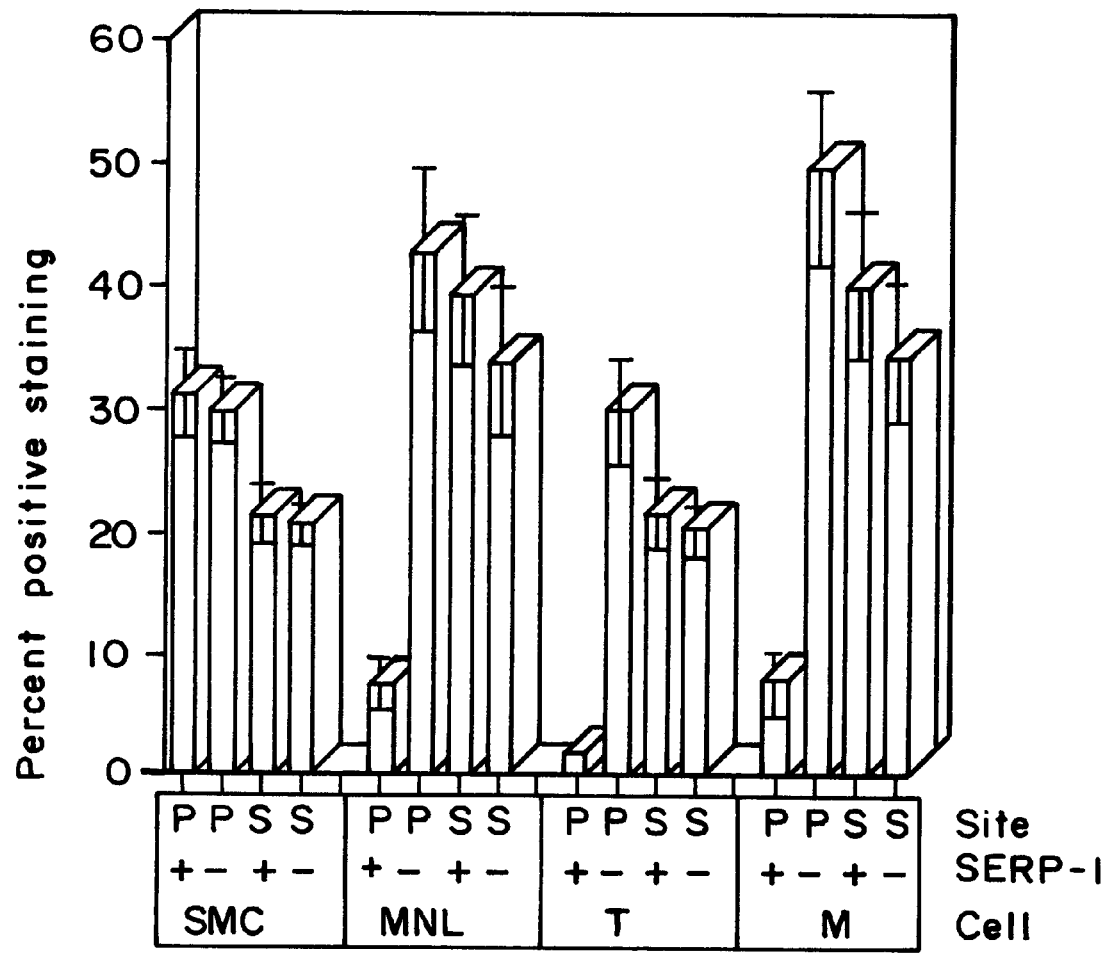

FIG. 5A is a bar graph demonstrating relative cellular populations detected at primary and secondary sites 24 hours after balloon injury and Wolinsky catheter infusion of SERP-1 in rabbit aorta. The primary (P) site refers to the site of Wolinsky infusion of purified SERP-1 (+) or saline (−) and secondary (S) site is an upstream balloon damaged but non-infused area in the upper thoracic artery. The cell populations stained were smooth muscle cells (SMC), CD11b positive mononuclear leukocytes (MNL), T lymphocytes (T), and macrophage (M).

Figure 5B:
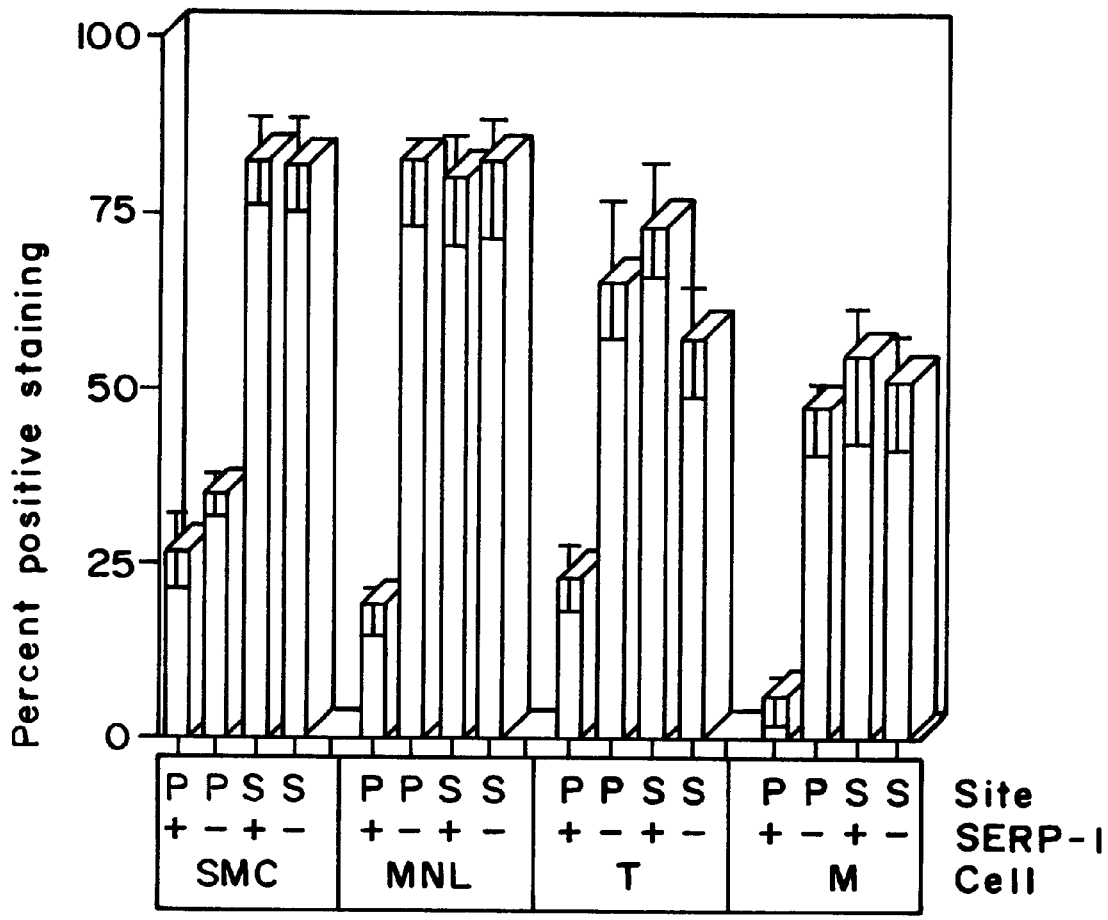

FIG. 5B is a bar graph demonstrating relative cellular populations detected at primary and secondary sites 4 weeks after balloon injury and Wolinsky catheter infusion of SERP-1 in rabbit aorta. The primary (P) site refers to the site of Wolinsky infusion of purified SERP-1 (+) or saline (−) and secondary (S) site is an upstream balloon damaged but noninfused area in the upper thoracic artery. The cell populations stained were smooth muscle cells (SMC), CD11b positive mononuclear leukocytes (MNL), T lymphocytes (T), and macrophage (M).

Figure 6A:

FIG. 6A shows a section of rabbit synovial tissue (obtained at stage B) exhibiting synovial inflammation four weeks after intra-articular administration of TGF beta 2 and ovalbumin in a saline treated animal.

Figure 6B:
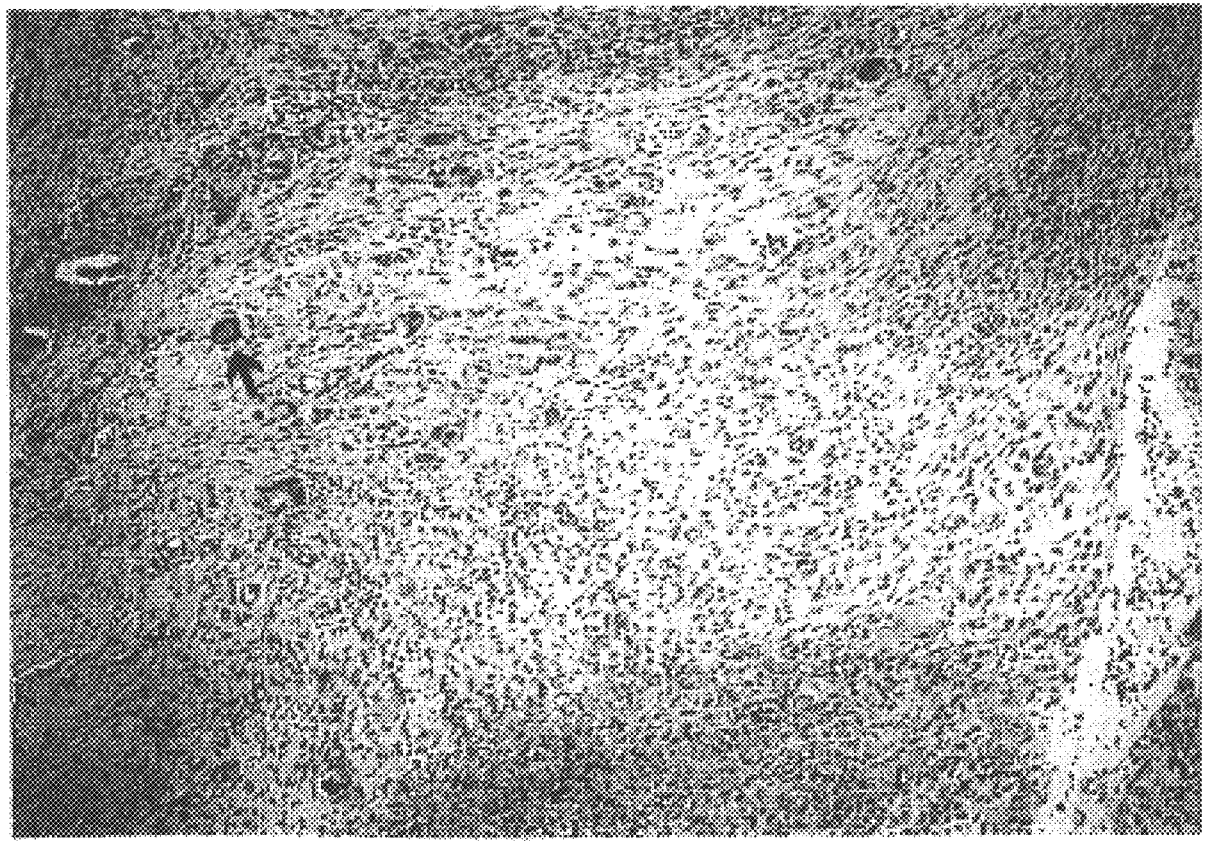

FIG. 6B shows a section of rabbit synovial tissue (obtained at stage B) exhibiting synovial inflammation and giant cell (arrow) four weeks after intra-articular administration of TGF beta 2 and ovalbumin in a saline treated animal.

Figure 7:

FIG. 7 shows a section of rabbit synovial tissue exhibiting resolution of synovitis in stage B SERP-1 treated animals six weeks after intra-articular administration of TGF beta 2 and ovalbumin.

DETAILED DESCRIPTION OF THE INVENTION

In accordance with the present invention, it has been surprisingly discovered that the protein SERP-1, a serine protease inhibitor produced by malignant rabbit fibroma virus (MRV) and myxoma virus (MYX), its analogs and biologically active fragments thereof, inhibit, prevent and reduce infiltration of inflammatory cells in injured and diseased tissues and in animals besides the rabbit for clinical manifestations that are of non-viral origin. The present invention therefore, is useful for preventing, inhibiting, and/or ameliorating inflammatory and immune reactions associated with various injury and disease conditions.

More specifically, in accordance with the present invention, a therapeutically effective amount of SERP-1, SERP-1 analogs or biologically active fragments thereof are administered to a subject in need of such treatment for a time and under conditions sufficient to prevent, inhibit, and/or ameliorate the inflammatory or immune reactions. The term "subject" as used herein is taken to mean any mammalian patient to which the compositions of the invention may be administered. Subjects specifically intended for treatment with the compositions and methodologies of the present invention include humans, as well as non human primates, sheep, horses, cattle, goats, pigs, dogs, cats, rabbits, guinea pigs, poultry, hamsters, rats and mice, as well as the organs, tumors and cells derived or originating from these hosts.

The present invention, therefore, is useful for treatment of a variety of clinical conditions involving inflammatory pathologies such as asthma. Asthma is characterized by the hyper-responsiveness of the tracheobronchial tree to various stimuli such as allergens, exercise, temperature, chemicals and spores. The most common asthma is atopic or allergic asthma and involves an immediate response due to mast cell histamine release and release of inflammatory modulators which recruit eosinophils, neutrophils and lymphocytes. The acute reaction results in bronchoconstriction, edema, increased mucus secretion, flushing, and in some cases hypotension. A late phase reaction four to eight hours later, lasting up to 24 hours, occurs due to the presence of the large population of recruited inflammatory cells which release further mediators of bronchoconstriction leading to edema and epithelial damage.

Adult respiratory distress syndrome (ARDS) is also treatable with the compositions and methodologies of the present invention. ARDS is an inflammatory condition characterized by increased capillary permeability, interstitial and intra-alveolar edema, fibrin exudation and formation of hyaline membrane. Inflammatory cells and mediators including leukocytes, cytokines, oxygen radicals, complement and arachidonate metabolite damage capillary endothelium and allow fluid and protein to leak across capillaries.

The present invention is also useful for preventing, inhibiting and/or ameliorating inflammatory and immune reactions associated with systemic lupus erythematosus (SLE). SLE is a classical multisystem autoimmune disease characterized by the presence of tissue damage due to self antigen directed antibodies. Autoantibodies bound to antigens in various organs lead to complement-mediated and inflammatory cell mediated tissue damage. Skin, connective tissue, blood vessels, and joints are all effected in this chronic, remitting and relapsing disease, but kidney failure due to antibody mediated glomerulonephritis is the main life-threatening complication. The present invention is useful in treating other autoimmune disorders such as scleroderma, various forms of vasculitis, inflammatory autoimmune myositis, and autoimmune thyroiditis.

The compositions and methodologies of the present invention are also efficacious in the treatment of multiple sclerosis (MS). M.S. is characterized by the penetration of the blood-brain barrier by circulating leukocytes, leading to demyelination in various parts of the brain, impaired nerve conduction and, ultimately, paralysis. Certain T cell clones reactive to myelin basic protein localize in the central nervous system and initiate inflammation.

The present invention is also efficacious for treatment of different forms of inflammatory arthritis. There are many different types of arthritis clinically recognized, the most common being rheumatoid arthritis. However, the inflammatory pathway relevant to the pathogenesis of rheumatoid arthritis is also likely relevant to the pathogenesis of other types of arthritis e.g. osteo, psoriatic and spondyloarthropathies since the synovial pathologies in all these forms of arthritis is in many cases, the same.

In the aforementioned embodiments of the invention, the SERP-1, SERP-1 analog or biologically active fragment thereof is delivered in a manner consistent with conventional methodologies associated with treatment of asthma, systemic lupus erythematosus, inflammatory autoimmune myositis, autoimmune thyroiditis, multiple sclerosis and arthritis such as for example, intravenously, intra-articularly, intrarectally, intraperitoneally, intramuscularly, subcutaneously, or by aerosol inhalant in order to prevent inflammatory and immune reactions associated with such diseases.

The present invention is useful for treating many other clinical conditions involving inflammatory processes. For example, inflammatory bowel diseases including Crohn's disease and ulcerative colitis are spontaneous chronic inflammations of the gastrointestinal tract which involve activation of inflammatory cells whose products cause tissue injury. Neutrophils, eosinophils, mast cells, lymphocytes and macrophages contribute to the inflammatory response.

Psoriasis which is characterized by, among other symptoms, epidermal hyperplasia/thickening and minute microabcesses of neutrophils in the upper epithelial layers of the dermis, is also treatable by the compositions and methodologies of the present invention. Psoriasis is believed to be caused by an autoimmune inflammatory response to a set of antigens in the skin. An increased autologous T cell response is seen in cells derived from a psoriatic lesion.

The present invention is also directed to treatment of systemic shock and many resultant clinical conditions associated therewith. Systemic shock often occurs as a complication of severe blood loss, severe localized bacterial infection, ischemia/reperfusion trauma and is a major cause of death in intensive care units. Most cases of septic shock are induced by endotoxins (i.e., bacterial cell wall lipopolysaccharides or LPS) from gram negative bacilli or toxins (i.e., toxic shock toxin 1) from gram positive cocci bacteria. The release of LPS in the bloodstream causes release of inflammatory mediators (inflammatory cytokines, platelet activating factor, complement, leukotrienes, oxygen metabolites, and the like) which cause myocardial dysfunction, vasodilation, hypotension, endothelial injury, leukocyte adhesion and aggregation, disseminated intravascular coagulation, adult respiratory distress syndrome (ARDS), liver, kidney and central nervous system (CNS) failure. Shock due to blood loss also involves inflammatory mediator release. In each case, inflammatory responses are induced at the original site of trauma, and also in the vasculature and remote vascularized sites.

Myocardial ischemia is associated with activation of the complement system which further promotes cardiac injury with the enhancement of a series of inflammatory events. Life threatening local and remote tissue damage occurs during surgery, trauma and stroke when major vascular beds are deprived for a time of oxygenation (ischemia), then restored with normal circulation (reperfusion). Reperfusion injury is characterized by vascular permeability leading to edema and infiltration of inflammatory cells. Neutrophils contribute significantly to reperfusion damage by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs. The compositions and methodologies of the present invention are useful in the treatment of ischemia and reperfusion injury.

Inflammatory response damage also occurs in glomerulonephritis as well as tubule disease. Infiltration of inflammatory cells (especially macrophages) is linked to proteinuria accompanied histologically by hypercellularity and crescent formation in glomeruli. Over a longer term, the infiltration of inflammatory cells is associated with accumulation of extracellular matrix and sclerosis and chronic compromise of renal function. The present invention is also efficacious in treating glomerulonephritis and tubule disease.

There are many other disease and injury conditions which benefit from the Compositions and methodologies of the present invention such as for example, coronary arterial occlusion, cardiac arrhythmias, congestive heart failure, cardiomyopathy, bronchitis, acute allergic reactions and hypersensitivity, neurotrauma, graft/transplant rejection, myocarditis, insulin dependent diabetes, and stroke.

In accordance with the present invention, the aforementioned disease and injury conditions are treated by administering the SERP-1, SERP-1 analog or biologically active fragment thereof in a manner consistent with conventional methodologies associated with treatment of the relevant injury or disease condition such as for example, intravenously, intra-articularly, intraperitoneally, topically, intrarectally, intra-arterially, intramuscularly, subcutaneously or by aerosol inhalant in order to inhibit or ameliorate inflammatory and immune reactions associated with such disease and injury conditions.

In accordance with the present invention, the SERP-1 protein, SERP-1 analog or biologically active fragment thereof, is first isolated and purified so that contaminants are removed. In a preferred method of producing the SERP-1 protein, analog or biologically active fragment of the present invention, a deoxyribonucleic acid (DNA) molecule or segment that defines coding sequence for, i.e., is capable of expressing a SERP-1, SERP-1 analog, or biologically active fragment thereof is used. DNA for SERP-1 can be isolated from MRV and MYX and related viruses using conventional means. A SERP-1 nucleotide and corresponding amino acid sequence is published (Upton et al., 1990 Virology 179: 618–631) and is also shown in FIG. 1 (SEQ. ID. NO.: 1).

Myxoma virus can be obtained from the American Type Culture Collection (ATCC), Catalogue No. VR-115. DNA may be extracted from the myxoma virus by methods well known in the art. The entire SERP-1 ORF or fragment thereof can be amplified by well known methods such as the polymerase chain reaction (PCR). In this way the entire SERP-1 ORF or a part thereof is obtained. A DNA molecule that includes a DNA sequence encoding the subject protein can also be prepared by operatively linking appropriate restriction fragments from various plasmids which are described elsewhere. See e.g., Upton, et al., 1990 Virology 179: 618–631; Macen et al., 1993 Virology 195: 348–363. Also contemplated by the present invention are ribonucleic acid (RNA) equivalents of the above described molecules. Thus the SERP-1, SERP-1 analog or biologically active fragment thereof is produced by a recombinant DNA molecule which includes a vector operatively linked, for replication and/or expression to coding sequence for the subject SERP-1 protein. As used herein, the term "vector") refers to a DNA molecule capable of autonomous replication in a cell and to which another DNA segment can be operatively linked so as to bring about replication of the attached segment. Vectors capable of directing the expression of a gene delivered by a subject DNA segment are referred to as "expression vectors".

One method of producing the subject protein of the present invention is by a vector comprising a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, an expression vector includes a prokaryotic promoter capable of directing the expression (transcription and translation) of the subject SERP-1 protein, SERP-1 analog or biologically active fragment thereof. Promoter sequences compatible with bacterial hosts are typically provided in plasmid vectors containing convenient restriction sites for insertion of a DNA segment coding for the subject SERP-1 protein, analog, or biologically active fragment thereof. A typical example of such a bacterial expression vector is pEX29, which utilizes the pL promoter (Klinkert et al., 1985 *Infection and Immunity* 49:329; Remaut et al., 1981 Gene 15:81) and allows expression in an *E. coli* host strain such as for example, W3110 (ATTC Accession No. 27325).

Preferred expression vectors for the production of SERP-1, SERP-1 analog or biologically active fragment thereof are compatible with eukaryotic cells, and preferably compatible with mammalian cells. Expression of the SERP-1, SERP-1 analog or biologically active fragment thereof in eukaryotic cells is preferred since such cells are able to glycosylate the SERP-1 protein. In some mammalian expression vectors, the SERP-1 DNA sequence may contain alterations to inactivate cryptic splice sites which preclude accurate expression of SERP-1 messenger RNA. Eukaryotic cell expression vectors are well known in the art and are available from several commercial sources. Typically, such vectors comprise convenient sites for insertion of a desired DNA segment. Examples of commercially available expression vectors with convenient restriction sites are pSVL, and pKSV-10 (Pharmacia), pBPV-1pML2d (IBI) and pTDT1 (ATCC Accession No. 31255). Other preferred vectors include pSAB132 and pJOD-S and derivatives pMDR901 and pMDR902 (Barsoum, 1990 *DNA and Cell Biology* 9:292; Miller et al., 1993 *J. Exp. Med.* 178:211.

The expression vectors compatible with eukaryotic cells and used to construct SERP-1 expression vectors for the production of SERP-1 protein can include a selection marker that is effective in a eukaryotic cell, preferable a drug resistance selection marker. An example of a drug resistance marker is neomycin resistance, obtained through expression of the neomycin phosphotransferase gene.

Preferred eucaryotic host cells include yeast, insect and vertebrate cells, preferably mammalian cells such as those from mouse, rat, monkey, or human fibroblastic cell line. Examples of eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. Transformation methods of procaryotic cells are described in Cohen et al., Proc. Natl. Acad. Sci. USA, 69:2110 (1972). Transformation of eucaryotic host cells including vertebrate cells are described in Sambrook et al., 1989 Molecular Cloning: A Laboratory Manual, Cold Spring Harbor Laboratories, Cold Spring Harbor, N.Y.; and Barsoum, 1990 *DNA and Cell Biology* 9:292; Barsoum 1995 (in press) *Methods in Molecular Biology XX: Electroporation Protocols*, Ed Nickoloff, Humana Press Inc., Totowa, N.J.

Successfully transformed cells, i.e., cells which contain a recombinant DNA molecule coding for SERP-1, SERP-1 analog or biologically active fragment thereof can be identified by well known techniques. For example, cells resulting from the introduction of rDNA vectors containing coding sequences for SERP-1, SERP-1 analog, or biologically active fragment thereof can be cloned and amplified to produce monoclonal colonies. Cells from those colonies can be harvested, lysed and their DNA content analyzed for the present of SERP-1 DNA using a method such as that described in Southern, *J. Mol. Biol.*, 98–503 (1975) or Brent et al., Biotech., 3: 208 (1985).

Besides directly assaying for the presence of SERP-1 DNA, successful transformants can be confirmed by well known immunological methods when the rDNA is capable of directing the expression of the subject protein. Cells successfully transformed with an expression vector comprised of coding sequences for SERP-1 produce secreted SERP-1, SERP-1 analog or biologically active fragments thereof. Samples of cells suspected of being transformed are harvested and assayed for the presence of SERP-1 antigenicity using anti-SERP-1 antibodies.

In one aspect of the invention, BV12-10a, an M13 clone used in sequencing the myxoma virus BamHI U3 fragment (Upton et al., 1990 *Virology* 179:618–631) which contains the intact SERP-1 ORF (SEQ ID NO:1) is grown in *E. coli* CJ236 ($dut^-$, $unq^-$). The procedures and methodologies employed in the Upton et al. reference are herein incorporated by reference. Oligonucleotide directed mutagenesis is performed as described in Kunkel et al., 1987 *Methods Enzymology*, 154:367–382, in order to insert a BamHI site directly 5' to the SERP-1 initiation codon (GGATCCATG). The resultant phage is propagated in E. coli JM103. A 1301-bp BamHI/HindIII fragment from this phage, containing the intact SERP-1 ORF is subcloned into pMTL22 (Chambers et al., 1988 Gene 68: 139–149). A 1344-bp BamHI/BgII fragment is then ligated into the BamHI site of the vaccinia expression plasmid pMJ601 (Davidson et al., 1990 Nucleic Acids Res. 18: 4285–4286) allowing SERP-1 to be inserted into the TK gene of vaccinia virus under the control of a strong, synthetic late promoter. Recombinant vaccinia virus (strain WR) is selected on TK$^-$ H143 cells in the presence of 25 µg/mL BUdR and plaque purified. Expression of the SERP-1 protein from the recombinant virus (designated WV-S1) is confirmed by immunoblotting using anti-SERP-1 antiserum. Control virus (not containing the SERP-1 ORF) is prepared by generating TK-recombinants of vaccinia WR using the parental pMHJ601 plasmid.

SERP-1 produced from VV-S1 is harvested from the supernatants of monkey BGMK cells twenty four hours after infection with virus at a multiplicity of infection of 1 pfu per cell as described. (Macen et al., 1993 Virology 195:348–363.) The procedures and methodologies employed in the Macen et al. paper are herein incorporated by reference.

In order to collect and purify the secreted SERP-1 glycoprotein produced in VV-S1, the growth medium containing the secreted viral proteins is collected, clarified by centrifugation and dialyzed against 25 mM Tris pH 8.0 and protein may be concentrated, for example with an Amicon Centriprep-10 apparatus. The dialyzed samples are then loaded onto a MonoQ column (Pharmacia) and protein is eluted using a linear salt gradient (0–300 mM NaCl). SERP-1 protein purified in this fashion is semi-purified. Preferably, the SERP-1 protein is then further purified by Superdex-75 column chromatography. SERP-1 protein further purified in this fashion is considered to be more highly purified and exhibits a higher biological activity.

SERP-1 containing fractions may be analyzed by sodium dodecyl sulfate polyacrylamide gel electrophoresis (SDS-PAGE). Total protein concentrations can be determined by well known methods such as Bradford assay. Protein concentrations may also be adjusted and determined by densitometric scans of silver stained gels or Western blotting using bacterially expressed SERP-1 protein as control standards. The control vaccinia vector lacking the SERP-1 ORF can also be harvested and purified from the BGMK cell supernatant in an identical matter.

After purification to a semi-pure or preferably to the more highly purified state, SERP-1 may then be admixed with sterile water and saline or other pharmaceutically acceptable carrier to a concentration in the range of between 1 pg/ml and 10 mg/ml and preferably between 1 pg/ml and 1 ug/ml. Alternatively, the SERP-1, SERP-1 analog, or biologically active fragment thereof, may be stored as a lyophilized powder, or frozen, and then later solubilized in sterile water or saline or other pharmaceutically acceptable carrier to the above delineated concentrations.

The SERP-1 of the present invention may be administered to a human patient preferably as a pharmaceutical composition in a therapeutically effective amount. The pharmaceutical compositions of the present invention contain a therapeutically effective dose of the SERP-1 protein, homologs or analogs thereof or else contain a biologically active fragment of the SERP-1 protein, homologs or analogs thereof together with a pharmaceutically acceptable carrier. The term "therapeutically effective amount" means the dose needed to effectively treat cellular infiltration and attendant cytokine network alterations associated with a variety of inflammatory diseases and injuries. For purposes of the present invention, the terms "treat" or "treatment" include preventing, inhibiting, reducing the occurrence of and/or ameliorating the physiological effects of the inflammatory condition treated.

As used herein, "analogs" is meant to include substitutions or alterations in the amino acid sequence of the SERP-1 protein, which substitutions or alterations (e.g., additions and deletions) maintain the anti-inflammatory properties of the protein when delivered to the site of inflammation either directed at the site, i.e. locally, or systemically. For purposes of the present invention, the term "analog" includes amino acid insertional derivatives of SERP-1 such as amino and/or carboxyl terminal fusions as well as intrasequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place. Where the protein is derivatized by amino acid substitution, amino acids are generally replaced by other amino acids having similar physical chemical properties such as hydrophobicity, hydrophilicity, electronegativity, bulky side chains and the like. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between glycine and serine. Additionally, the substitution of a basic residue such as lysine, arginine or histidine for another or the substitution of an acidic residue such as aspartic acid or glutamic acid for another is also contemplated.

As used herein, the term "analogs" also encompasses homologs of SERP-1, i.e., corresponding amino acid sequences derived from other SERP-1 proteins and having the same or substantially the same anti-inflammatory properties. As used herein, the term "biologically active fragments" refer to fragments of SERP-1 or SERP-1 analogs which do not encompass the entire length of the SERP-1 polypeptide but which nevertheless maintain the anti-inflammatory properties of the entire SERP-1 polypeptide or analogs thereof when delivered to the site of inflammation either at the site (i.e. locally) or systemically.

SERP-1 amino acid variants may be readily made using peptide synthetic techniques well known in the art such as solid phase peptide synthesis (Merrifield synthesis) and the like or by recombinant DNA techniques well known in the art. Techniques for making substitution mutations at predetermined sites in DNA include for example M13 mutagenesis. Manipulation of DNA sequences to produce substitutional, insertional, or deletional variants are conveniently described elsewhere such as Sambrook et al., 1989 Molecular Cloning: A Laboratory Manual, Cold Spring Harbor Laboratories, Cold Spring Harbor, N.Y.

For purposes of the present invention, analogs of SERP-1 also include single or multiple substitutions, deletions and/or additions of any component(s) naturally or artificially associated with the SERP-1 such as carbohydrate, lipid and/or other proteinaceous moieties. All such molecules are encompassed by the term SERP-1 analogs.

In one embodiment of the invention, in order to increase the specific activity of the prepared SERP-1 protein, the cysteine residue at position 244 may be substituted with another amino acid residue, for example alanine. Such a substitution causes the SERP-1 protein to be more biologically active since $CyS_{244}$ is the predicted position for SERP-1 dimer formation through disulfide bridges. Because $Cys^{244}$ lies very close to the reactive center of the SERP-1 protein, SERP-1 dimers are thought to have a disturbed and obfuscated reactive center thereby rendering them biologically inactive. Lomas et al., 1993 J. Biol. Chem. 268 (1): 516–521. A mutation at position 244 prevents the formation of SERP-1 dimers in the production of SERP-1 through recombinant DNA means. A decrease in the presence of SERP-1 dimers in a preparative sample is useful since the specific activity of the isolated protein will be increased and thus less protein will be needed in a pharmaceutical preparation.

The inhibitory activity of serpins on serine proteinases is believed to revolve around the slow dissociation of the serpin from the serine protease after cleavage of the serpin between the P1 and P1' residues in the active region. Upton et al., 1990 Virology 179: 618–631. The amino acid sequence Arg/Asp has recently been located at the predicted SERP-1 P1-P1' site (amino acid residues 319 and 320) and is the predicted site for cleavage by serine proteases. Substitutions of either or both of these two amino acids produces SERP-1 analogs of varying biological activities useful in the practice of the present invention.

The formulation of pharmaceutical compositions is generally known in the art and reference can conveniently be made to Remington's Pharmaceutical Sciences, 17th ed., Mack Publishing Co., Easton, Pa. Formulation of the SERP-1 protein, analogs, or fragments thereof for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of SERP-1 suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject SERP-1 is accomplished by incorporating these compounds in the required amount in the appropriate solvent with various ingredients enumerated above, as required, followed by sterilization, preferably filter sterilization. To obtain a sterile powder, the above solutions are vacuumdried or freeze-dried as necessary.

The subject SERP-1 protein or analogs and fragments thereof, are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients (SERP-1, SERP-1 analogs and fragments thereof). The use of such media and agents for pharmaceutical active substances is well known in the art. Supplementary active ingredients may also be incorporated into the compositions and used in the methods of the present invention.

The precise therapeutically effective amount of SERP-1 protein, analog or fragment thereof to be used in the methods of this invention applied to humans can be determined by the ordinarily skilled artisan with consideration of individual differences in age, weight, extent of cellular infiltration by inflammatory cells and condition of the patient. It can generally be stated that the SERP-1 pharmaceutical preparation of the present invention should be preferably administered in an amount of at least about 30 pg per infusion dose, more preferably in an amount up to about 300 mg per dose.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on the unique characteristics of the active material (e.g., SERP-1 protein, SERP-1 analogs, or fragments thereof), and the limitations inherent in the art of compounding such an active material for the treatment of cellular infiltration as herein disclosed in detail.

The principal active ingredient is compounded for convenient and effective administration in effective amounts with a suitable pharmaceutically acceptable carrier in dosage unit form as hereinabove disclosed. A unit dosage form can, for example, contain the principal active compound in amounts ranging from 30 pg to about 30 mg. In the case of compositions containing supplementary active ingredients, the dosages are determined by reference to the usual dose and manner of administration of the ingredients.

Packaging material used to contain the SERP-1 active ingredient can comprise glass, plastic, metal or any other suitable inert material so long as the packaging material does not chemically react with any of the ingredients contained therein.

The SERP-1 protein, analogs or fragments thereof may be administered in a manner compatible with the dosage formulation and in such amount as will be therapeutically effective. The compositions of the invention may be administered in any way which is medically acceptable which may depend on the disease condition or injury being treated. Possible administration routes include injections, by parenteral routes such as intravascular, intravenous, intraarterial, subcutaneous, intramuscular, intratumor, intraperitoneal, intraventricular, intraepidural or others, as well as oral, nasal, ophthalmic, rectal, topical, or by inhalation. The compositions may also be directly applied to tissue surfaces during surgery. Sustained release administration is also specifically included in the invention, by such means as depot injections or erodible implants.

The invention is further illustrated by the following specific examples which are not intended in any way to limit the scope of the invention.

EXAMPLE 1

Purification of myxoma SERP-1 Protein

The vaccinia vector (VV-S1) that over expresses myxoma SERP-1 has been described previously (Macen et al., 1993 *Virology* 195:348–363) and the procedures and methodologies employed in Macen et al. are herein incorporated by reference. SERP-1 protein was harvested from the supernatant of BGMK cells infected with VV-S1 and purified by column chromatography. Cells in roller bottles were adsorbed with VV-S1 or VV-601 (control virus which does not express SERP-1) for 1–2 hours at 37° C., washed with phosphate buffered saline, and incubated with Dulbecco's modified Eagles' medium (15 ml/bottle) without serum. After 24 hours, the medium was harvested, clarified at 10,000 g for ten minutes, concentrated 10× with a centriprep 10 (Amicon) concentrator, dialyzed against 25 mM Tris-HCl, pH8.0, and loaded onto a MonoQ (Pharmacia) column. Proteins were eluted with a linear 0–1.0 M NaCl gradient and fractions containing SERP-1 were identified by sodium dodecyl sulfate polyacrylamide gel electrophoresis (SDS-PAGE) and immunoblotting using anti-SERP-1 antiserum (Macen et al. 1992 *Virology* 195:348–363), and loaded onto a Superdex G-75 (Pharmacia) FPLC column equilibrated with 25 mM Tris-Cl, pH8.0, 150 mM NaCl. Vaccinia vector control proteins secreted from cells infected with a vaccinia construct lacking SERP-1 (VV-601) were purified in parallel with recombinant vaccinia that over expresses SERP-1 (VV-S1). The foregoing purification scheme provided SERP-1 purified to apparent homogeneity (FIG. 2, lane 3).

EXAMPLE 2

Infusion of SERP-1 at the Site of Balloon Mediated Injury

Thirty-eight rabbits (strain New Zealand white) were fed a 2% cholesterol in 10% peanut oil diet four days a week, for two weeks prior to balloon angioplasty which was performed as follows. A 3–3.5 mm angioplasty balloon catheter (≧1:1 ratio of balloon to aorta diameter) was introduced via femoral arterial cut down following anesthetic (40 mg/kg ketalean, 8 mg/kg xylene, and 0.5 mg/kg acepromazine by intramuscular injection). The balloon was inflated to 8 bars pressure in the distal abdominal aorta and advanced retrograde to the distal thoracic aorta. The balloon was advanced and withdrawn three times under fluoroscopic control in each rabbit to ensure endothelial denudation. Heparin (400 units) was given immediately after obtaining femoral access to decrease catheter associated thrombosis.

Superdex G-75 purified SERP-1 (FIG. 2, lane 3) at protein doses of 30 pg to 30 ng per sample was infused immediately after balloon mediated injury in the distal abdominal aorta. Control animals were administered a similar volume of saline solution. Each infusate was administered via Wolinksy catheter as previously described (Stadius et al. 1993 *Am. Heart J.* 126:47–55; Wolinsky et al., 1990 *J. Am. College Cardiol.* 15:475–481; Santonian et al., 1993 *Cath. Cardiovascular Diag.* 30:348–354) in a total volume of 10 ml diluted in sterile 0.9% saline immediately following balloon mediated injury. All infusions were via a 3.25 mm Wolinsky balloon (inflated to a final pressure of 6±1 bars for two minutes) in the abdominal aorta proximal to the iliac bifurcation. The Wolinsky balloon was positioned immediately above the iliac bifurcation under fluoroscopic control such that the perfusion balloon was routinely located from 0.5 to 2.5 cm above the bifurcation and designated as the primary infusion site. Upstream secondary sites were defined in the region above 2.5 cm proximal to the iliac bifurcation.

EXAMPLE 3

Immunohistochemical Analysis of SERP-1 and Control Treated Tissues

Immunohistochemical staining was used to determine changes in cellular populations at vascular sites of intimal injury in the rabbit aorta after SERP-1 and saline infusion as described in Example 2. Two time points were chosen for analysis: 24 hour post-infusion samples were used to assess the level of acute cellular infiltration in response to the Wolinsky infusion and four weeks post-infusion samples were used to evaluate chronic responses. The rabbit cell populations measured were vascular smooth muscle cells (anti-actin antibody) mononuclear leukocytes (anti-CD 11b antibody), activated T lymphocytes (anti-CD 25 antibody) and macrophages (RAM11 antibody).

Immunohistochemical analysis was performed at the primary site of Wolinsky infusion in the distal abdominal aorta representing the primary infusion site as defined by the original positioning of the perfusion balloon and at upstream secondary sites defined in the region above 2.5 cm proximal to the iliac bifurcation using the methods described in Gown et al. 1986 *Am. J. Pathol.* 125:191–207. In brief, formalin fixed aortal sections were cut into 5 $\mu$m sections and stained using the indirect peroxidase labeled antibody technique as described in Naish S. J., ed. 1989 *Handbook of Immunochemical Staining methods*, Dako Corp., Carpinteria, Calif. Paraffin sections were taken from formalin fixed rabbit aorta and immunostained with Sigma diagnostics (St. Louis, Mo.) mouse anti-alpha human smooth muscle actin antibody for smooth cells (which cross reacts with rabbit smooth muscle cells), with rat anti-mouse CD-11b monoclonal antibody that cross reacts with rabbit (Spring Valley Laboratories Inc., Woodbine, Md.) for rabbit mononuclear cells, with mouse anti-rabbit CD25 specific monoclonal antibody (Spring Valley Laboratories Inc.) for activated rabbit T lymphocytes, and with mouse ascites RAM11 monoclonal antibody (obtained from E. Raines, U. Washington,. Seattle) for rabbit macrophages. Each primary antibody-treated section was then incubated with biotinylated goat anti-mouse or anti-rat antibody for 30 minutes and avidin biotin peroxidase complex (ABC) for 40 minutes. Each section was developed with DAB for five minutes. Negative controls for each staining procedure were carried out by substituting the primary and/or secondary antibody with neutral buffered saline. Positive controls consisted of human arterial smooth muscle cells and rabbit small bowel (for alpha-actin), rabbit tonsil and spleen (for CD11b) and rabbit tonsil (for CD25). Each section was incubated with 20% normal goat serum prior to primary antibody addition to decrease nonspecific staining. The percentage positive staining was determined by assessing 3–5 representative high power areas per slide and quantifying the number of positive grids divided by the number of squares in the grid covered by the area of intimal hyperplasia or media.

The sections which displayed acute responses 24 hours after infusion showed no significant differences in smooth muscle cell numbers at primary sites of SERP-1 infusion (FIG. 3A) versus saline control (FIG. 3B), but significant reductions in the infiltration of CD11b$^+$-mononuclear cells (FIGS. 3C and 3D) activated T lymphocytes (FIGS. 3E and 3F) and macrophages (FIGS. 3G and 3H) into primary sites perfused by purified SERP-1 protein were observed as compared to the saline controls. When comparable sections from infusion sites were stained for these same cell populations at four weeks post-infusion, a similar profile was observed for smooth muscle cells (FIGS. 4A and 4B), but marked reductions were again observed for CD11B$^+$-mononuclear cells (FIGS. 4C and 4D), activated T lymphocytes (FIGS. 4E and 4F) and macrophages (FIGS. 4G and 4H). In order to compare the effect of SERP-1 infusion on cellular infiltration at primary infused sites in the same animal, the percent positive staining cells for each of the four antibodies was quantitated for primary and secondary sites. As shown in FIG. 5A, at 24 hours post-infusion there were no significant differences in smooth muscle cell (smc) populations at either primary or secondary sites whereas reductions in the infiltration of CD 11b-positive mononuclear leukocytes (MNL), CD25-positive T cells (T) and macrophages (M) were restricted to the primary (P) sites of SERP-1 infusion, but not saline controls, and were not observed at secondary (S) sites in either case. When the same analysis was performed on four weeks samples (FIG. 5B), no major effect of SERP-1 was observed on smooth muscle cell population in plaque but the chronic levels of infiltration of CD11b-positive mononuclear leukocytes, CD25-positive T cells, and macrophages remained low at the sites of primary SERP-1 infusion as compared to any of the secondary sites. Thus, by 24 hours after SERP-1 infusion there was a significant decrease in the influx of CD11b-positive mononuclear cells (p<0.0001), CD-25 positive T lymphocytes (p<0.0001), and RAM11 positive macrophages (p<0.003) on comparison with saline infusion at sites of primary Wolinsky infusion or any of the secondary sites. Similarly, in the chronic samples, mononuclear cell (p<0.0004), activated T cell (p<0.0037), and macrophage (p<0.0001) staining remained significantly decreased at four weeks follow up at sites of primary SERP-1 infusion both in the body of the intimal plaque and in the deeper medial layers of the vessel wall.

These results demonstrate several findings as to the protective mechanism of SERP-1 protein at perfused sites. At the primary site of SERP-1 infusion, there is a dramatic decrease in the local infiltration of reactive inflammatory leukocytes within the first 24 hours after SERP-1 infusion which is followed by a decrease in chronic inflammatory cell infiltration that persists until at least 4 weeks after SERP-1 infusion. SERP-1 therefore, down regulates pro-inflammatory signals directly at the primary infusion site.

EXAMPLE 4

Treatment of antigen-induced arthritis (AIA) with SERP-1

Fifteen rabbits (Charles River, Canada) weighing 2.5 to 3.0 kg were anesthetized with Rompun cocktail (ketamine, rompun, acepromazine) and immunized with 10 mg of ovalbumin emulsified with an equal volume of Freund's complete adjuvant (Sigma) given intramuscularly and subcutaneously in several sites in the nape of the neck. Two weeks later, all rabbits received an intraarticular (IA) injection of 1 mg of ovalbumin and 1 ml of sterile, pyrogen-free, saline solution. Observation two weeks after IA injection revealed minimal clinical evidence for arthritis. Consequently, two consecutive daily IA injections of 5 mg of ovalbumin and 65 ng of recombinant human transforming growth factor (TGF) beta 2 (Genzyme) were administered into a hind limb joint to facilitate the induction of arthritis as described in Fava et al. 1991 *J. Exp. Med.* 173:1121–1132. One rabbit died on the second day during induction of anesthesia and post-mortem examination revealed a congenital heart defect. Synovial histology of remaining rabbits revealed extensive inflammation with PMN infiltration, prominent vasculitis, and areas of fibrinoid necrosis.

The remaining 14 animals were randomly allocated to one of three groups: Group A received 0.5 ml of sterile pyrogen-free saline by IA injection. Group B received 100 pg of purified SERP-1 protein by IA injection, and Group C received 1 ng of the SERP-1 protein by IA injection. IA injections were given two weeks after the last IA injection of ovalbumin and TGF beta and in the same hind limb joint as the ovalbumin and TGF beta injection. Two weeks after IA injection of SERP-1, two animals from each group were sacrificed by administering sodium phenobarbital (100 mg per kg). Synovial fluid counts were obtained and synovial tissue removed for histologic analysis (Stage A). The remaining animals in each group were given a second IA injection of either saline or SERP-1 at the previously administered dosage. Animals were sacrificed two weeks later and synovial histology performed (Stage B).

To assess the severity of the chronic arthritis in SERP-1 treated and untreated rabbits, the synovial membranes were excised and samples fixed in buffered formalin and processed for routine histology. At least three synovial specimens were analyzed to compensate for any variation in the degree of synovitis within a particular joint. Gross and histopathologic findings were assessed blindly and assigned qualitative characteristics as listed in Table I. Differences among experimental groups were tested using the U-Mann Whitney test.

Synovial histology of Stage A treated animals revealed a diminution in synovial fluid PMN count and histology score in comparison to saline controls (Table II). This finding was more pronounced in animals which received a 100 pg dose of SERP-1.

Macroscopic inspection of the joints in animals which received at least two IA injections of either saline or SERP-1 (Stage B treated animals) revealed marked diminution in synovial hypertrophy and articular cartilage erosion in SERP-1 treated animals (Table III) which appeared to be more evident with the 1 ng (P=0.05, one tailed test vs. saline controls) rather than the 100 pg dosage (P=0.2 vs saline controls)(Table III). Cartilage erosions were observed in only one of the five joints of treated animals six weeks post intra-articular injection of antigen as opposed to two out of three saline-treated animals. Macroscopic changes correlated with synovial histology and a dose-response effect was apparent. FIGS. 6A and 6B illustrate synovial inflammation in saline-treated animals with giant cell formation. In contrast, FIG. 7 illustrates resolution of synovitis commonly observed in SERP-1 treated animals. No toxicity was observed in treated animals.

These results demonstrate that administration of purified SERP-1 in an animal model of arthritis correlated with human chronic synovitis results in a considerable diminution in chronic inflammatory cell infiltration as well as a considerable diminution in the degree of synovial hyperplasia and cartilage erosion.

TABLE I

Assessment of Antigen-induced Arthritis

A: GROSS POSTMORTEM
   0:  Normal joint
   1:  increased joint fluid, no apparent synovial thickening/ inflammation
   2:  synovial thickening/inflammation to 1 mm
   3:  synovial thickening/inflammation 1–3 mm
   4:  synovial thickening/inflammation to 4 mm, perisynovial granulation tissue
   5:  any of 1–4 above with erosion of joint cartilage
B: HISTOLOGY
   Synovial lining layer hyperplasia (0 to 3+)
   Intensity of subsynovial cellular infiltrate (0 to 3+)
   Presence of neutrophil infiltrate (0 to 3+)
   Pannus tissue +(3) or –(0)
   Cartilage erosion +(3) or –(0)

TABLE II

Synovial fluid cell counts and histology scores.
Effects of
treatment with one IA injection of SERP-1 in established AIA*

| Treatment | Animal | Synovial Fluid PMN per mm$^3$ | Histology Score** |
|---|---|---|---|
| Saline | 1 | 4510 | 18 |
|  | 2 | 6578 | 23 |
| SERP-1 | 1 | 484 | 11 |
| 100 pg | 2 | 2.2 | 6 |
| SERP-1 | 1 | 1716 | 13 |
| lng | 2 | 121 | 14 |

*Raw data per animal
**Total for 3 synovial specimens per joint

TABLE III

Macroscopic and histologic scores.
Effects of
treatment with two IA injections of SERP-1 in established AIA*

| Treatment | Animal | Macroscopic Score | Histology Score** |
|---|---|---|---|
| Saline | 1 | 4 | 22 |
|  | 2 | 5 | 20 |
|  | 3 | 5 | 14 |
| SERP-1 | 1 | 3 | 15 |
| 100 pg | 2 | 4 | 13 |
| SERP-1 | 1 | 2 | 7 |
| lng | 2 | 2 | 7 |
|  | 3 | 3 | 13 |

*Raw data per animal
**Total for 3 synovial specimens per joint

EXAMPLE 5

Effect of SERP-1 on Inflammation and Heart Failure Associated with Coronary Arterial Occlusion Coronary arterial occlusion with resultant lack of blood flow to the heart, ischemia, and ensuing myocardial damage and necrosis is induced in mongrel dogs by the following procedure. Under sterile conditions, mongrel dogs (28–35kg) are anaesthetized using intravenous pentobarbital (30–35 mg/kg) and maintained using a continuous infusion of pentobarbital at a rate of approximately 0.05 mg/kg per minute. Succinylcholine (1 mg/kg) is also given intravenously at the time of anaesthesia induction. The animals are then intubated with a cuffed endotracheal tube and ventilated with warm, humidified room air and oxygen through a ventilator such as the Siemens 900 ventilator. A femoral line is inserted and systemic pressure is continuously displayed. Arterial blood samples are drawn periodically to maintain pH, $PO_2$, and $pCO_2$ within physiological limits. Body temperature is maintained at 37° C. with warmed humidified ventilated air and a heat lamp placed over the thorax. Temperature is monitored using a YSI 73A temperature controller (Yellow Springs Instrument Company, Yellow Springs, Ohio) that has a thermistor positioned in the mid-esophagus. Electrocardiographic leads are applied for continuous ECG monitoring. Ten day old and four week old infarcts are created as follows. The heart is exposed under sterile conditions through a limited (4 cm) left thoracotomy at the fourth intercostal space. The pericardium is opened to expose the proximal left anterior descending (LAD) artery and is dissected as proximal to its origin as possible and a nose occluder is applied. Partial occlusion is maintained for thirty minutes and complete occlusion is maintained for ninety minutes. The nose occluder is removed and reperfusion is allowed to occur. A chest tube is inserted and the chest closed in layers. Animals are allowed to recover for four to ten days. In order that an accurate comparison is made between normal and infarcted hearts, control dogs (which are divided into groups that either receive SERP-1 infusions or are not infused) are subjected to sham LAD occlusion to eliminate possible obfuscating factors secondary to LAD occlusion as well as surgery, thoracotomy, pericardiotomy, adhesions and the like.

After ten days, SERP-1, at doses ranging from 3 pg/kg to 3 mg/kg, is given by coronary arterial infusion to monitor the effect on inflammation and heart failure in dogs with induced coronary occlusions. Similar doses of SERP-1 are administered by intra-peritoneal (i.p), subcutaneous (s.c.) and intravenous administration (iv).

Dogs are monitored at selected time intervals over a 2–6 month follow up. Echocardiography is used to assess left ventricular function. Routine Hematoxylin and eosin staining of the myocardium is used to monitor the effect of SERP-1 on myocardial inflammation. Immunohistochemical staining of myocardium as described in Examples 3 and 4 is used to monitor the effect of SERP-1 on myocardial infiltration by inflammatory cells. Chavanash et al., 1992 *Circulation* 85:680–698.

EXAMPLE 6

Effect of SERP-1 on induced cardiac arrhythmias

Dogs with induced arterial occlusions (Example 5) are allowed to recover for six, thirty and sixty days and then subjected to a second surgery for induction of cardiac arrhythmias. After pentobarbital anesthesia similar to that of the first surgery (Example 5), a second surgical procedure is commenced. A midline sternotomy and pericardial cradle is performed with similar hemodynamic monitoring and intravenous infusions as in Example 5. An anodal titanium mesh defibrillation patch electrode (Medtronics TX-7, reduced to 4.5 sq. cm.) is sutured to the right atrium/superior vena cava junction. A cathodal defibrillation patch (Medtronics TX-7, 15 sq. cm.) is sutured to the left ventricular apex. Intervention shocks as well as therapeutic defibrillation shocks are administered by positioning a third titanium mesh defibrillation patch electrode (Medtronics TX-7, reduced to 4.5 sq. cm.) in the area of the RV outflow tract. The aortic root fat pad is dissected free and a 4.0 mm Ag/AgCl reference electrode is sutured to the aortic root to serve as the reference for all DC coupled unipolar recordings. For the initial global epicardial mapping of voltage gradient fields and activations, an epicardial jacket containing uniformly positioned and easily re-positionable tripolar button electrodes is fitted around the heart. After global mapping to confirm the sites of early activation, a greater density of recording electrodes is concentrated over the early activation sites including the infarct and border zones. Previously described transmural and septal recording electrodes may also be used for voltage gradient determinations throughout the heart. After all electrodes are placed, the heart is draped with a 4×4 sponge moistened with warm saline. The sternum is approximated and draped with a plastic sheet and a moist towel to maintain the heart in a moist and constant temperature environment. Ventricular fibrillation is induced by 60 Hz alternating current outside and inside the infarct zone as well as by rapid ventricular pacing in the infarct zone.

SERP-1 at doses ranging from 3 pg/kg to 3 mg/kg, is given by coronary infusion on the day of arterial occlusion surgery or at follow up to monitor the effects on global alteration in the passive properties of conduction as well as lethal ventricular arrhythmias. Time course of change in the passive properties of myocardial conduction in response to administration of SERP-1 is determined using microscopic endocardial recordings and correlated with deterioration in LV function and the development of ventricular arrhythmias. Wikowski et al., 1993 *Circulation Research* 72:424–439.

EXAMPLE 7

Effect of SERP-1 on Congestive Heart Failure and Cardiomyopathy

Congestive heart failure and cardiomyopathy is induced in mongrel dogs as follows. Under sterile conditions, mongrel dogs (28–35kg) are anaesthetized using intravenous pentobarbital (30–35 mg/kg) and maintained using a continuous infusion of pentobarbital at a rate of approximately 0.05 mg/kg per minute. Succinylcholine (1 mg/kg) is also given intravenously at the time of anaesthesia induction. A pace maker is inserted into the right ventricular area of the heart and set on a high rate ranging from 100 to 280 beats per minute. After 14–30 days, SERP-1, at doses ranging from 3 pg/kg to 3 mg/kg, is given either by coronary infusion, intra-peritoneal (i.p), subcutaneous (s.c.) or intravenous administration (iv). Dogs are monitored for effect of SERP-1 on myocardial inflammation and heart failure at selected time intervals over a 2–6 month follow up. Echocardiography is used to assess left ventricular function. Routine hematoxylin and eosin staining of myocardium is used to monitor the effect of SERP-1 on myocardial inflammation. Immunohistochemical staining of myocardium is used to monitor the effect of SERP-1 on myocardial infiltration by inflammatory cells. In addition, confocal and electron microscopy studies are performed to monitor differences in spatial distribution and molecular characteristics of gap junctions in SERP-1 treated myopathic and normal hearts.

EXAMPLE 8

SERP-1 Treatment of Conditions Associated with Acute Pulmonary Inflammation

Sensitization of Animals

Sprague-Dawley rats, aged 8–12 weeks are sensitized two weeks before SERP-1 treatment with 1 mg ovalbumin (OA) grade V and 200 mg $Al(OH)_3$ in 1 ml saline (subcutaneous administration) and 1 ml Bordetella pertussis vaccine ($2\times10^9$) bacilli (intraperitoneal administration) as adjuvant to potentiate IgE antibody production. Sprague-Dawley rats thus sensitized are used for monitoring the effects of SERP-1 on conditions associated with hyperactive airways such as asthma and bronchitis.

Sprague-Dawley rats infected with the nematode *Nippostronqylus brasiliensis* are used to monitor the effects of SERP-1 on acute allergic reactions specifically related to the pulmonary system such as allergy and hypersensitivity. *N. brasiliensis* sensitized rats, valuable in monitoring allergen-induced pulmonary inflammation, including local neutrophilia, eosinophilia and alveolar macrophage recruitment and function are described in detail in Ramaswamy et al., 1991 *J. Parasitology* 77:302–312 and Mathison et al., 1992 *Br. J. Pharmacology* 106:263–266, incorporated herein by reference.

SERP-1 Administration and Effects on Acute Pulmonary Inflammation

SERP-1 is administered at selected times after sensitization (Bordetella pertussis vaccine or *N. brasiliensis*) by aerosol, subcutaneous, intraperitoneal or intravenous infusions at doses ranging from 3 pg to 3 ug total dose per experimental animal. Sensitized rats are also administered the same volume of saline solution as an experimental control. The effect of SERP-1 treatment is monitored by histology and immunohistochemical analysis (performed as in Example 3) of tissue from pulmonary specimens.

In order to monitor effects of SERP-1 on alveolar macrophage functions, sensitized rats and in some cases sensitized rats which have also undergone SERP-1 infusion as described above are exposed to aerosols using the following procedure. Aerosols are generated using the Wright nebulizer from Roxon Medi-Tech Lte (Montreal, PQ) using compressed air with a pressure giving an output of 0.1–0.2 ml/min passed into a plexiglass box. Saline or OA (2% in saline) is nebulized for five minutes to anesthetized rats, thereby delivering Ag in aerosol form.

After exposure to aerosols, SERP-1 is administered via aerosol or subcutaneous, intraperitoneal, or intravenous infusions at doses ranging from .3 pg to 3 mg total dose per experimental animal. Aerosol exposed rats are also administered a comparable volume of saline solution as an experimental control. After 0, 6, 10, 30, 60 and 90 days, rats weighing between 190–250 g are anesthetized, the trachea exposed and cannulated with a metal tracheal cannula to which are brazed three other metal tubes. One tube connects to a pressure transducer (such as a Validyne MP45+/−50 $cmH_2O$) for measuring airway pressure. The other two tubes which form a "Y" allow connection to the inspired and expired pathways of a ventilator such as the Harvard Rodent Ventilator. The ventilator is set to deliver a tidal volume of 8 to 10 ml/kg at a rate of 50–60 breaths per minute.

After the surgical preparation, each tracheotomized rat is placed in a 30×15×10 cm plastic box and the trachea connected to the ventilator and to the airway pressure transducer. The ventilator is started and the box lid closed. Both the airway pressure and the box pressure are directed to a computer and stored in Lotus 1,2,3. Measurements are taken over ten second periods during which the results from 7–10 complete tidal breaths are collected. The box pressure signal represents volume changes due to ventilation and the signal is differentiated to provide inspired and expired flow rate. A spreadsheet is therefore generated which provides data for airway pressure, tidal volume and tidal flow. From this data, respiratory system resistance and dynamic compliance (or elasticity) is calculated, thereby providing a measure of degree of bronchoconstriction for both control (saline infused) and experimental (SERP-1 infused) rats.

Sheep are known to develop both early and late bronchial responses to inhaled *Ascaris suum* antigen and are thus useful in monitoring SERP-1 effects on inflammatory conditions such as asthma and bronchitis. See Abraham et al., 1993 *Am. Rev. Respir. Dis.* 128:839–844 and Abraham et al., 1994 *J. Clin. Invest.* 93:776–787, incorporated herein by reference. After topical anesthesia of the nasal passages, a balloon catheter is advanced through one nostril into the lower esophagus and the animals intubated with a cuffed endotracheal tube through the other nostril. Pleural pressure is measured with the esophageal balloon catheter filled with about 1 ml air. Lateral pressure in the trachea is measured with a catheter adjacent to the tip of the 1O endotracheal tube and both pleural and tracheal catheters are connected to a differential pressure transducer such as the Validyne MP45, Northridge, Calif. Transpulmonary pressure is determined as the difference between the two pressures. Airflow is measured by connecting the proximal end of the endotracheal tube to a pneumotachograph (Fleis, Dyna Sciences, Inc., Blue Bell Pa.). Pulmonary flow resistance is determined as the temporal change in transpulmonary pressure divided by the change in airflow at mid-tidal volume. Bronchoalveolar lavage is performed using a fiberoptic bronchoscope with aliquots of pH 7.4 buffered saline.

Antigen (typically *Ascaris suum* extract, obtainable from Greer Diagnostics, Lenoir N.C.) is introduced via a conventional medical nebulizer connected to a dosimeter system comprising a solenoid valve, a source of compressed air and a respirator.

Baseline airway response characteristics and bronchoalveolar lavage is performed several days prior to an experimental run. On the day of the experiment, airway responsiveness is again measured and then myxoma SERP-1 is introduced via intravenous infusion of about 3 pg/kg to 3 mg/kg or an equivalent volume of saline. After administration of SERP-1, airway responsiveness (specific lung resistance, mean pulmonary flow resistance and the like) are assayed and the animal is then challenged with antigen. Post challenge determinations of airway responsiveness and post challenge bronchoalveolar lavage are made at various times after antigen challenge. Control and polypeptide trials are separated by at least three weeks, a time interval sufficient for the sheep to recover from past challenges. In another protocol, the effect of administering SERP-1 after antigen challenge is monitored.

In vitro parameters measured to assay the effectiveness of SERP-1 include differential cell counts in the lavage fluid of epithelial cells, macrophages, lymphocytes, neutrophils, basophils, eosinophils and monocytes.

Guinea pigs may also be monitored for the effects of SERP-1 on hyperactive airways such as asthma. See eq., Pretolani et al. 1994 *J. Exp. Med.* 180:795–805. Male Hartley guinea pigs are sensitized by aerosolized albumin (Miles, Naperville, Ill.). The procedure is repeated 48 hours later and the animals are exposed to challenge by ovalbumin aerosol solutions 14–17 days after the first inhalation. Control animals are sensitized as above but are exposed to saline after 14–17 days. SERP-1 polypeptide is administered to sensitized guinea pigs, about 1 hour before and about 4 hours after antigen challenge.

The effect of SERP-1 polypeptide administration on antigen-induced bronchial hyperactivity and cellular infiltration is assayed in a number of ways. Changes in bronchial resistance to lung inflation are measured by a pressure transducer placed between the trachea and a respiratory pump and continuously recorded on a dynograph. Bronchial reactivity is tested by repeated administration of methacholine (Sigma Chemical Co.). Alliquots of arterial blood are collected for total leukocyte counts using a Coulter counter and for differential counts after staining. Bronchoalveolar cells are collected in successive lavages using aliquots of sterile saline injected and recovered through a polyethylene tracheal cannula. Differential cell counts and measurement of eosinophil peroxidase is also performed on the lavage fluids. Immunohistochemical studies are performed on dissected lung tissue previously fixed in chloroform acetone. Sections are stained with a variety of monoclonal antibodies specific for T cells, and activated eosinophils, using conventional techniques such as those described in Pretolani et al. 1994.

EXAMPLE 9

SERP-1 Treatment of Secondary Immune-Mediated Injury Following Neurotrauma

Reproducible injury of the thoracic spinal cord in Lewis rats is induced via an electromechanical impact device as described previously (Stokes et al. 1991 *J. Neurotrauma* 9:187–195; Popovich et al. (1993) *J. Neurotrauma* 10:37–46; Popovich et al. 194 *Brain Research* 633:348–352). Briefly, the electromechanical impact device is used to make brief contusive injuries to the rodent spinal cord (<25 msec total duration). The animals are routinely anesthetized with ketamine (60 mg/kg) and xylazine (10 mg/kg), and a single segment laminectomy is performed at spinal level T8 or T9. The spinal cords are contused with the device by rapid displacement of the spinal cord 1.1 mm from the original cord surface and both displacement and force are recorded continuously. Superficial wounds are then closed in layers and the injured animals allowed to recover.

Injured rats are administered SERP-1 via intravenous routes (0.3 pg to 3 mg dosages) and by intraspinal injections (0.3 pg to 3 mg dosages). Injured rats in a control group are administered a similar volume of saline solution. One, six, fourteen, thirty, sixty and ninety days after SERP-1 infusion, rats are sacrificed by administering sodium phenobarbital (100 mg per kg). The effects of SERP-1 treatment on progressive tissue necrosis following traumatic injury is monitored by histological, biochemical, immunological and behavioral criteria that are known to be associated with neurotrauma in Lewis rats. For example, parenchymal microglia from the central nervous system and infiltrating reactive leukocytes, known to mediate extensive cell death occurring post-trauma are monitored as follows.

Immunohistochemical analysis is performed on formalin fixed sections cut from injured regions of the thoracic spinal cord. Paraffin sections taken from the fixed rabbit spinal cord are immunostained with a variety of standardized cell surface markers such as MHC markers, CD markers for the specific cell subtypes, and the like which measure the extent of microglial activation and levels of leukocyte infiltration into the spinal parenchyma in the area of the contusion lesion produced by the spinal injury device. In addition, assessment of the local expression of standard inflammatory cytokines such as TNF, and IL1 is conducted by RT-PCR and Northern blotting analysis. Lymphocyte activation in the appropriate draining lymphoid tissues are measured by lymphocyte proliferation assays and by the adoptive transfer of spinal injury-activated lymphocytes.

EXAMPLE 10

Effect of SERP-1 on Inflammatory Bowel Diseases, Arthritis and Psoriasis

Transgenic rats expressing the human class I major histocompatibility allele, HLA-B27, (Hammer et al. 1990 *Cell*

63:1099–1112) are used to monitor the effects of SERP-1 on inflammatory bowel diseases, arthritis and psoriasis. Virtually all HLA-B27 rats develop chronic gastrointestinal inflammation by age 16 weeks while approximately 70% develop arthritis and a substantial number develop psoriasis during the same time frame. In addition, Cotton top tamarins (CTT) are also used to monitor the effects of SERP-1 on spontaneous and acute colitis resembling ulcerative colitis and Crohn's disease. See Podolsky et al., 1993 *J. Clin. Invest.* 92:372.

SERP-1 is administered to HLA-B27 rats and Cotton-top tamarins by a variety of routes: intravenous (0.3 pg-3 mg), subcutaneous (0.3 pg-3 mg), intraperitoneal (0.3 pg-3 mg) intra-articular (0.3 pg-3 mg), and intrarectal (0.3 pg-3 mg). After one to thirty days, tissue samples are collected for analysis of inflammatory parameters. After assessing SERP-1 effects, the number of SERP-1 injections is optimized as needed.

Macroscopic inspection of rat joints is performed as discussed in Example 4. Gut pathology of HLA-B27 mice and Cotton-top tamarins is graded macroscopically and microscopically using established criteria of inflammation such as those enumerated in Table IV, adapted from Kellen et al. 1986 *Radiation Res.* 105:84–96. SERP-1 effects on psoriasis are monitored by examining psoriatic lesions and observing changes in scale numbers, epidermal thickening, hyperplasia and staining for the associated inflammatory cells (mostly lymphocytes) in the mouse.

Inflammatory bowel disease in rabbit is induced by colonic administration of trinitobenzene sulfonic acid (TNBS) as described in Percy et al., 1993 *Gastroenterology* 104:369–376 or chemotactic peptide, f-met-leu-phe as described in LeDuc et al., 1990 *Gastroenterology* 98:929–935. New Zealand white rabbits (3–4 kg) are anesthetized by intramuscular administration of xylazine and ketamine. A Foley catheter is inserted approximately 15 cm into the colon and inflated with 3 ml of air and gently withdrawn to induce muscular clearance of distal fecal matter. A dialysis bag (8–10 cm, n.7, 10 mm diameter, Spectrum Medical Industries, Houston, Tex.) with 3–4 ml of 150 mg/ml TNBS in 50% ethanol is inserted into the distal colon and left in place for one hour. The bag is then removed and animals are treated with intravascular, intraperitoneal, intramuscular, subcutaneous or suppository delivered SERP-1 (3 pg/kg to 3 mg/kg) or saline control. Treatment is either in a single dose immediately following TNBS removal, one hour following TNBS removal, one day following TNBS removal or daily for five days following TNBS removal. Animals are euthanized with pentobarbital (60 mg/kg) 5 days post-TNBS treatment. The distal 5 cm of colon is analyzed for inflammatory bowel disease. Hematoxylin and eosin stained colon tissue sections are evaluated for the appearance of the lamina propria, submucosa, muscularis mucosae and mucosa with respect to ulceration, crypt abscesses, neutrophil aggregation and the presence of inflammatory infiltrate in the muscularis propria. Colitis is defined as the presence of acute and chronic inflammatory cells in the lamina propria and acute intraepithelial inflammatory cells.

TABLE IV

MORPHOLOGICAL PARAMETER*

Crypt depth, μm
Villus height, μm
Villus width at ½ height, μm
Villus bottom width, μm
Villus surface area μm²/villus
No. of cells/villus
No. of villi/mm serosal length
No. of villi/mm² serosa
Mucosal surface area mm²/mm² serosa
Microvillus height, μm
No. of microvilli/μm

EXAMPLE 11

Effect of SERP-1 on psoriasis

In addition to using HLA-B27 rats as discussed in Example 10, the effects- of SERP-1 on psoriasis are monitored in mice carrying the flaky skin (fsn) mutation. Psoriatic lesions can also be maintained as skin grafts on normal littermates or nude mice so that the pathologic features of the fsn phenotype can persist independent of the host thymic-derived immune system. Sundberg et al., 1944, *J. Invest. Dermatol.*, 102:781–788.

SERP-1 is administered to fsn/fsn mice or normal littermates or nude mice carrying a skin grafts from fsn/fsn mice by a variety of routes: intravenous (0.3 pg-3 mg), subcutaneous (0.3 pg-3 mg), intraperitoneal (0.3 pg-3 mg) and intra-articular (0.3 pg-3 mg). After 0, 6, 14, 30, 60 and 90 days, tissue samples are collected for analysis of inflammatory parameters. After assessing SERP-1 effects, the number of SERP-1 injections can be increased as needed.

SERP-1 effects on psoriasis are monitored by examining psoriatic lesions and observing changes in scale numbers, epidermal thickening, hyperplasia and staining for the associated inflammatory cells (mostly lymphocytes) in the mouse. Epidermal hyperplasia is measured as an increase in DNA synthesis, estimated by detecting increased $^3$H-thymidine uptake into cells of psoriatic lesions.

The measurement of autoreactive T cell activation by antigen presenting cells from human psoriatic lesions is also used to monitor SERP-1 effects on human psoriatic cell function in vitro. Epidermal cell suspensions are prepared from fresh skin biopsies of normal individuals and individuals suffering from psoriasis. T cells from the same individuals are purified simultaneously, and the epidermal cells containing the antigen presenting cells are co-cultured with autologous, CD4-positive T cells from the same individual to initiate T cell activation. Autoreactive responses are assessed using conventional methods such as, for example, measuring uptake of tritiated thymidine or by quantitation of relative amounts of mRNA for lymphokines such as IL-2, gamma interferon and IL-4.

The ability of SERP-1 to diminish various antigen presenting cells in the lesional (or normal) skin in activating T cells or in activating distinct types of cytokines, is examined by directly adding SERP1 to the cell/T cell culture. Inhibition of tritiated thymidine uptake within the antigen presenting cell/T cell co-culture indicates SERP-1 inhibition of the autoreactive process. These data are compared with results obtained with buffer and normal skin cell controls.

EXAMPLE 12

Effects of Serp-1 on Graft/Transplant Rejection

Male Cynomolgus monkeys which have received heterotrophic renal allografts during ketamine hydrochloride/ diazepam anesthesia (Cosimi et al. 1990 *J. Immunoloqy* 144:4604–4612) are used to monitor the effects of SERP-1 in ameliorating graft rejection. SERP-1 therapy is commenced on the day of transplantation or at appropriate times thereafter. SERP-1 is administered by a variety of routes: intravenous (3 pg-3 mg), subcutaneous (3 pg-3 mg), intraperitoneal (3 pg-3 mg) and intra-articular (3 pg-3 mg). Allografts are serially sampled by open wedge biopsy at approximately weekly intervals beginning the week after transplantation. Autopsies are performed at the time of death and heart, liver, lungs, spleen, lymph nodes and the allograft are sampled. Samples are either fixed in buffered 4% formalin and routinely processed for microscopic study or else frozen at −70° C. for immunoperoxidase analysis.

Tissue section samples are examined microscopically and scored for cellular infiltration by counting the number of infiltrating mononuclear cells in a square grid using two to four random fields. Extent and degree of infiltration, proliferation or necrosis of the arterial endothelium and media is noted in control (no SERP-1 treatment) and experimental samples.

SERP-1 effects are also monitored by assaying the expression of leukocyte antigens including intracellular adhesion molecule-1 (CD54) and ICAM-1 in vascular endothelium of the kidneys and other organs using well known methodologies such as FACS analysis and immunohistochemical staining.

Lewis male rats are also used to monitor the effects of SERP-1 on mediating graft rejection. (LEW×BFN)$F_1$ hearts are transplanted heterotopically into the abdominal cavity of LEW recipients as described previously (Paul et al., 1992 *Transplantation* 53:157). Recipient rats are randomized to receive either no treatment (control) or SERP-1 infusions administered by a variety of routes: intravenous (3 pg-3 mg), subcutaneous (3 pg-3 mg), intraperitoneal (3 pg-3 mg) and intra-articular (3 pg-3 mg). Extent of interstitial cellular infiltration is characterized by immunocytochemistry using the macrophage mAb ED1, ED2, ED3 AND EG5 (a monoclonal antibody that reacts with T lymphocytes and a subpopulation of B cells). See Paul et al., 1992, *Transplantation* 53:157.

In another method of monitoring the effects of SERP-1 on ameliorating graft rejection, New Zealand White rabbits are subjected to interposition vein grafting of the carotid artery. Beginning 0, 6, 30, 60 and 90 days after surgery, animals are randomly assigned to a control or SERP-1 treated group. SERP-1 infusions are administered by a variety of routes: intravenous (3 pg-3 mg), subcutaneous (3 pg-3 mg), intraperitoneal (3 pg-3 mg) and intra-articular (3 pg-3 mg). Animals are sacrificed and vessels harvested for intimal hyperplasia analysis. Intimal hyperplasia in the carotid arteries and vein grafts from both experimental and control samples is measured by computerized image analysis as discussed in Wilson et al., 1994 *Eur. J. Vas. Surg.* 8(1):60–64.

SERP-1 ameliorative effects on thrombus formation is also measured by administering SERP-1 to pigs having thrombogenic vascular grafts interposed in arteriovenous shunts. The porcine vascular graft/arteriovenous shunt has been previously discussed in Scott et al., 1994 *Circulation* 90(4):1951–1955. SERP-1 routes of administration, dosages and thrombus measurements are essentially the same as discussed above.

EXAMPLE 13

Effects of SERP-1 on myocarditis

Autoimmune myocarditis is induced in Lewis rats by immunization with cardiac myosin fraction as discussed previously in Kodoma et al., 1994 *Circ. Res.* 75 (2): 278–284.

Immunized rats are randomly assigned to a control or SERP-1 treated group. SERP-1 infusions are administered by a variety of routes: intravenous (3 pg-3 mg), subcutaneous (3 pg-3 mg), intraperitoneal (3 pg 3 mg) and intra-articular (3 pg-3 mg). Animals are sacrificed and hearts removed for routine histological and immunological analysis. SERP-1 modulating effects on autoimmune myocarditis are monitored by noting reduced size and discoloration in hearts from SERP-1 treated animals on comparison to untreated control animals and noting reduced ratios of heart weight to body weight in hearts from SERP-1 treated animals on comparison to untreated control animals. In addition, SERP-1 ameliorative effects on myocardial muscle loss and replacement fibrosis are also measured by radionuclide assessment and thermodilution dye assessment of cardiac output as well as routine hemodynamic measurements and myocardial weight.

Viral myocarditis is induced in mice by infection with Coxsackievirus B3 (rCVB3) as discussed previously in Zhang et al., 1994 *Int. J. Exp. Pathol.* 75(2):99–110. SERP-1 modulating effects on myocarditis are monitored as discussed above.

EXAMPLE 14

Effect of SERP-1 on Insulin Dependent Diabetes

Splenocytes from non-obese diabetic (NOD) mice showing signs of diabetes are harvested and red-cell depleted in parallel with splenocytes from nondiabetic mice as described in Burkly et al., 1994 *Diabetes* 43:529–534. Splenocytes from NOD mice are (a) pre-treated with SERP-1 or (b) pre-treated with nonspecific, isotype-matched immunoglobulin or (c) untreated. Splenocytes are then injected intravenously (2–3×$10^7$ cells in 0.2 ml PBS) into nondiabetic mice. Controls include nondiabetic mice receiving buffered saline or splenocytes from nondiabetic mice.

In an alternative procedure, SERP-1 is administered 0, 6, 14, 30, 60, and 90 days after splenocyte transfer rather than used in pre-treatment of splenocytes from NOD mice. SERP-1 infusions are administered by a variety of routes: intravenous (3 pg-3 mg), subcutaneous (3 pg-3 mg), intraperitoneal (3 pg-3 mg) and intra-articular (3 pg-3 mg). SERP-1 ameliorative effects on diabetes are monitored by routine assays for urine and plasma glucose levels. Animals are sacrificed and pancreases harvested in 10% formalin PBS for paraffin-embedded sectioning followed by hematoxylin and eosin staining for histology. Islets are scored in a blind experiment and at least 25 islets are examined per individual animal. Degree of insulitis is scored as described in Burkly et al., 1987: grade 0, no insulitis; grade I, peri-insulitis; grade II, the lesion of cell infiltration occupies less than 25% of the islet area; grade III, 25–50% infiltrated and grade IV, more than 50% infiltrated. The percentage of uninfiltrated islets (grade 0), moderately infiltrated islets (grade I-II) and severely infiltrated islets (grade III-IV) is calculated in relation to the total number of islets monitored for each individual animal.

EXAMPLE 15

Effect of SERP-1 on Stroke

The modulating effect of SERP-1 on central nervous system ischemia is monitored using gerbils, rabbits or rats. Induction of single and repetitive-insult ischemia in gerbils has been described previously in Wishart et al., 1994 *Neuroreport* 5(12): 1541–1544.

Reversible spinal cord ischemia is induced in the rabbit by temporary occlusion of the abdominal aorta. Irreversible cerebral ischemia in rabbits is induced by injection of plastic microspheres (50 microns) into the internal carotid artery so that spheres lodge in the cerebral vasculature. See Bowes et al., 1994 *Stroke* 25 (11);2253–2257.

SERP-1 is administered after initiation of ischemia by either infusion at a dosage range of 3 pg to 3 mg per kg body weight or as an exchange transfusion at a dosage range of 3 pg to 3 mg per kg bodyweight. Effects of SERP-1 are monitored in the animals undergoing reversible ischemia by noting performance differences in a water maze task in SERP-1 treated and control treated animals. SERP-1 effects are monitored in animals undergoing irreversible cerebral ischemia by measuring the duration of ischemia required to produce permanent paralysis.

Focal ischemia is initiated in rats by occluding a cerebral artery as described in Davis et al., 1994 *Acta. Neurochir. Suppl.* 60:282–284. Prior to initiation of focal ischemia, rats are randomly assigned into an experimental group receiving SERP-1 pretreatment administered subcutaneously, intravenously, intra-arterially, intraperitoneally or into the spinal fluid at dosages of 0.3 pg to 300 ug or a control group receiving saline (or no pretreatment). SERP-1 effects are monitored by histological assessment of infarct volume and analysis of specific gravity as an index of cerebral edema using well known methodologies.

EXAMPLE 16

Effect of SERP-1 on Multiple Sclerosis

Experimental autoimmune encephalitis (EAE) is an MS-like syndrome and is induced by injecting experimental animals intraperitonealy with CD-4 positive T cell clones specific for myelin basic protein. Injected T cell clones reactive to myelin basic protein localize in the central nervous system and initiate inflammation. See Ben-Nun et al., 1981 *Eur. J. Immunol.*, 11: 195–199 ; Hickey et al., 1991 *J. Neurosci. Res.*, 28: 254–260, incorporated herein by reference. Endogenous monocytes and lymphocytes penetrate inflamed vessels in the brain stem and spinal cord.

EAE is induced by injecting about $8 \times 10^6$ cells of the appropriate T cell clone intraperitonealy into Lewis rats. Production and maintenance of the T-cell clone is as described in Ben-Nun et al., 1981 *Eur. J. Immunol.*, 11: 195–199. Rats typically develop hind limb and tail paralysis, within 4–5 days. Yednock et al. 1991 *Nature* 356: 63–66. Briefly, Lewis rats are immunized with myelin basic protein emulsified in saline and complete Freund's adjuvant. After about 9 days, draining lymph nodes are removed, resuspended in supplemented Eagle's medium, and cultured in petri dishes with added myelin basic protein. Lymphoblasts are then separated and concentrated in one step on a Ficoll density gradient. The lymphoblast fraction is recovered, washed and propagated in vitro in Eagle's medium supplemented with concanavalin-A stimulated spleen cells, horse serum, amino acids, pyruvate, 2-mercaptoethanol and antibiotics. T lymphocytes are selected by limiting dilution in microtiter wells containing irradiated syngeneic thymus cells and myelin basic protein. Ben-Nun et al., 1981.

SERP-1 ameliorative effects in M.S. can also be monitored in mouse Hepatitis virus (JHM coronavirus) infected mice. JHM is injected intracerebrally in young mice with subsequent disease progression (Lucas et al. 1979 *Cell* 12:553–560; Robb et al., 1979 *Virology* 94:352–370. SERP-1 is administered prior to, or simultaneously with, administration of the T-cell clone or with JHM strain infection. SERP-1 ameliorative effects on inflammation are monitored using routine hematoxylin and eosin and immunohistochemical staining and an in vitro adhesion assay previously described in Yednock et al. 1991 *Nature* 356:63–66. Sections of 5 day EAE or JHM infected brain are tested for the ability to support leukocyte attachment. Stamper and Woodruff, *J. Exp. Med.*, 144: 828–833, (1976). Leukocytes e.g. human monocytic cells of line U937, at a concentration of about $10^7$ cells $ml^{-1}$ are layered over freshly cut, unfixed 10 um sections of EAE rat brain exposed (experimental) or unexposed (control) to SERP-1. Attached leukocytes are discerned as more darkly stained than the sectioned brain tissue and located in a different focal plane.

SERP-1 ameliorative effects on cellular infiltration are monitored immunohistochemically using central nervous system sections taken from experimental and control treatments and a variety of available antibodies such as those enumerated in Table 1 of Yednock et al., 1992 *Nature*, 356: 63–66, incorporated herein by reference. The labeled antibody technique is described in Naish S. J., ed. 1989 *Handbook of Immunochemical Staining Methods*, Dako Corp., Carpinteria, Calif. For example, experimental and control sections are treated with monoclonal antibody OX-1, (against CD45 which is expressed on all leukocytes) or monoclonal antibody ED1 which recognizes circulating monocytes. Differences in numbers of reactive leukocytes and monocytes between control and experimental sections are noted.

EXAMPLE 17

SERP-1 Effects on Systemic Lupus Erythematosus (SLE)

NZB/NZW F1 hybrids and MRL (lpr/lpr) mice are two strains of mice which develop spontaneous SLE-like diseases. Female offspring of New Zealand Black/White crosses develop severe immune complex nephritis, anti-DNA antibodies and undergo severe generalized lymphocyte dysfunction within several months after birth and generally die before nine months. See Howie and Helyer 1968 *Adv. Immunol.* 9.:215, incorporated herein.

Similarly, MRL (lpr/lpr) mice develop fatal immune complex glomerulonephritis within six months of birth, accompanied by massive lymphoproliferation with enlarged peripheral lymph nodes and gross splenomegaly. About 10–20% of MRL mice also develop progressive rheumatoid arthritis and vasculitic skin lesions before death. See e.g. Theofilopolous and Dixon, 1985 *Adv. Immunol.* 37:269–390, incorporated herein by reference. Generally, mice younger than about ten weeks are disease free, and mice older than about 16 weeks develop the disease.

Beginning soon after birth, both strains of mice are administered SERP-1 at a dosage of lng to 3 pg/kg-3 mg/kg via intravenous and intraperitoneal routes staggered by time intervals varying from one week to one month. The effect of SERP-1 at ameliorating immune pathology associated with SLE is monitored monthly, using the following standardized criteria: (i) renal function manifested by proteinuria, urea levels in urine, glomerular filtration rates and levels of subcapsular renal hemorrhage; (ii) number of foci of glomerulonephritis in kidney sections; (iii) lymphocyte infiltration of lacrimal and parotid glands; (iv) levels of anti-erythrocyte and anti-DNA and anti-nuclear antibodies; (v) levels of IgM hypergamma globulinaemia; (vi) loss of thymic function, eg. IL-2 production from isolated lymphocytes; (vii) kidney morphology e.g. enlargement of glomerular deposits, (viii) increased plasma TNF/IL-6 and increased concanavalin A-induced and spontaneous cytokine secretion by T-cells.

The aforementioned criteria are measured by assays described in Morrow et al., 1987 *Autoimmune Rheumatic Disease*, Blackwell Scientific Pub., Oxford, incorporated by reference herein. SERP-1 administration is increased to multiple (weekly and monthly) injections as needed.

In an alternative murine model of SLE, mice are injected at birth with semi-allogenic lymphoid cells. Injected mice develop a lupus-like autoimmune syndrome in which donor B cells are polyclonally activated by host alloerotic CD4$^+$T cells, producing autoantibodies and immune complex mediated glomerulonephritis. See Ramos et al., 1994 *Immunology* 82:287–293, incorporated herein by reference. SERP-1 administration and monitoring of effects are as described above.

EXAMPLE 18

Effect of SERP-1 on Lung Injury

An animal model of acute lung injury (e.g. ARDS) is described in Doershuk, et al., 1990 *J. Immunol.* 144:2327–2333. SERP-1 ameliorative effects on lung injury is monitored as follows. First, New Zealand white rabbits weighing 1–4 kg are anesthetized with ketamine (25–40 mg/kg i.v.) and acepromazine maleate (2–3 mg/kg). Following tracheotomy, a narrow flexible tube is inserted and passed into the peripheral bronchus using fluoroscopy. Rabbits are treated with intravascular, intraperitoneal, subcutaneous, inhaled aerosolized SERP-1 at doses of 3 pg to 3 mg/kg (or saline control) 20 minutes prior to or 20 minutes following instillation of inflammatory stimuli. Pulmonary inflammation is induced by intrabronchial infusion of one of three types of stimuli: *S. pneumonia* (0.15 ml/kg, 10$^9$ organisms/ml saline with 7% colloidal carbon), hydrochloric acid (0.15 ml/kg, 10 ug/ml saline with 10% monsteral blue), or phorbol myristate acetate (25 ug/kg with 10% monasteral blue). The tube is then removed and the incision sutured. Pulmonary inflammation is monitored at 20 minutes, 1, 2, 4, 6, and 12 hours post inflammatory stimulus instillation by removal of the lung, preparation of tissue sections stained with eosin/hematoxylin and morphometric quantitation of PMN or PMN versus red blood cell (RBC) infiltration in alveoli. Catheters are removed during anesthesia (5–10 mg/kg ketamine with local 1% lidocaine). Animals are maintained under standard conditions in cages and are monitored daily for weight, Hct and arterial blood gases. At five days post-hemorrhage, the animals are euthanized by pentobarbital overdose and necropsy performed. Organs are examined for gross evidence of injury in tissue sections stained with hematoxylin and eosin. Lungs are analyzed histologically and bronchial alveolar lavage fluid is analyzed for cell counts nd leukocyte infiltration.

Animal models of septic and endotoxic shock are described in Harlan et al. 1992 *J. Applied Physiol.* 73(4):1510–1516. Using these models, 3 pg to 300 ug doses of SERP-1 are administered to animals prior to and/or following endotoxin infusion or appendectomy daily for three days via intravascular, intramuscular, subcutaneous, inhaled aerosol or intraperitoneal administration. SERP-1 efficacy in preventing shock is monitored in sacrificed animals from days 1 through 5 following endotoxin infusion or appendectomy using the above described methods.

An additional model of lung injury due to endotoxic shock in rats is described in Rabinovici et al., 1992 *J. Immunol.* 149:1744–1750 and SERP-1 administration and analysis of lung and organ injury is performed in this model as described above.

EXAMPLE 19

Effect of SERP-1 on Ischemia and Reperfusion Injury

Two models of local ischemia/reperfusion injury are described in Mihelcic et al, 1994 *Blood* 84:2322–2328 and Kelly et al, 1994 *Proc. Natl. Acad. Sci* 91:812–816. A local and remote ischemia/reperfusion injury model is described in Hill et al., 1992 *J. of Immunol.* 149:1723–1728.

New Zealand white rabbits (1.5 to 3 kg) are anesthetized with intravenous ketamine and xylazine. A peripheral ear vein is cannulated and a local nerve bloc accomplished by injection of lidocaine at the base of the ear. This ear is then transected at its base leaving intact only the central artery, central vein and a small portion of supporting cartilage. All nerves to the distal segment of the ear are cut, rendering the ear completely anesthetic. A microvascular clip is placed on the central artery of the left ear to produce complete ischemia. The ear is then reattached with suture and the microvascular clip allowed to exit through the wound. The ear is reperfused by removal of the clip after six hours. At the time of reperfusion, a bolus injection of SERP-1 at dosages of 3 pg/kg to 3 mg/kg is given either intravenous, intraperitoneal, subcutaneous or intramuscular. Ambient temperature between 23.5° C. and 24° C. is maintained throughout the procedure.

Injury manifested by edema is determined by submerging the ear into a beaker of water up to the suture line and measuring displacement. Tissue necrosis is determined as percentage necrotic area compared to total surface area. These measurements are performed by an unbiased observer. Neutrophil infiltration is measured using the myeloperoxidase assay using a tissue extract from the rabbit ear.

Male Sprague-Dawley rats weighing 1.6–1.9 kg are fasted for 12 hours prior to surgery. After sodium pentobarbital (65 mg/kg) and 6 ml 0.9% NaCl are administered for anesthesia, the renal artery and vein are surgically exposed and occluded bilaterally for 30 minutes with microaneurysm clamps. SERP-1 is administered in doses of 3 pg/kg to 3 mg/kg by intravenous, intraperitoneal, subcutaneous, or intramuscular injection upon release of the clamped renal vessels. At time points ranging from 0 to 72 hours post-reperfusion, tail vein blood samples are taken and analyzed for urea nitrogen (BUN), a standard urease assay/conductivity assay and creatinine using picric acid reactions. For histochemical analysis of injury, rats are sacrificed at time points from 0.5 to 72 hours and kidney tissue is fixed in formalin, sectioned and stained with hematoxylin and eosin. The percent of tubules in the outer medulla showing epithelial necrosis or necrotic debris is quantitated by blinded observers. Myeloperoxidase assays are performed on kidney tissue collected at time points ranging from 0.5 to 72 hours post-reperfusion to measure neutrophil infiltration.

EXAMPLE 20

Effect of SERP-1 on Renal Failure

Glomerulonephritis is induced by anti-glomerular basement membrane antibody in rat. WKY rats (300–350 kg) are anesthetized by intraperitoneal injection of ketamine (25–30 mg/kg) and sodium pentobarbital (50 mg/kg). SERP-1 in doses from 3 pg/kg to 3 mg/kg is administered either by intravascular, intramuscular, intraperitoneal or subcutaneous injection. Sheep anti-rat glomerular basement membrane IgG or control IgG (0–10 mg) is intravenously administered. Rats are then housed in metabolic cages for 24 hour intervals for up to 10 days following anti-GBM to measure proteinuria. Total urinary protein is measured using standard Lowry assays. Some animals receive in addition to the initial administration of SERP-1, daily doses of SERP-1 from 3 pg/kg to 3 mg/kg administered by intravascular, intramuscular, intraperitoneal or subcutaneous injection. Animals are sacrificed at various times and the kidneys removed, fixed, and sectioned. Hematoxylin and eosin stained or toluidine blue stained sections of renal tissue are analyzed for inflammatory cell infiltration, crescent formation, hypercellularity and sclerotic tissue. Extracellular matrix formations detected by staining with anti-fibronectin and anti-tenascin antibodies.

Another model of rat glomerular sclerosis in Sprague-Dawley rats using anti-thymocyte serum is described in detail in Okuda et al., 1990 *J. Clin. Invest.* 86:453–462. Using this model, SERP-1 is administered in doses from 3 pg/kg to 3 mg/kg by intravascular, intramuscular, intraperitoneal or subcutaneous injection on a daily basis following serum infusion for up to 7 days. Histological sections of renal tissue from 0 to 7 days post-serum infusion are stained with hematoxylin and eosin or anti-tenascin antibodies to determine gross injury, inflammatory cell infiltration and sclerosis.

EXAMPLE 21

Effect of SERP-1 on Systemic Shock

New Zealand white rabbits weighing 1–1.5 kg are anesthetized with ketamine (30 mg/kg i.v.). Under sterile conditions, central venous and thermistor-tipped aortic catheters (et. model 94–011, American Edwards Laboratories, Santa Ana, Calif.) are placed through an open femoral approach with local 1% lidocaine supplement. Arterial blood pressure (BP), central venous pressure and core temperature are monitored continuously. Periodic determinations are made of arterial blood gases, hematocrit (Hct), white blood cell count (WBC), and relative thermodilution cardiac output (CO) using a cardiac output/lung water computer (American Edwards Laboratories). After recovery from anesthesia, each animal is treated with intravenous, intramuscular, subcutaneous or intraperitoneal SERP-1 from 3 pg/kg to 3 mg/kg doses or saline control 30 minutes prior to and/or following hemorrhage. Hemorrhagic shock is accomplished by withdrawal of blood via the venous catheter into a heparinized (10 u/ml) polypropylene syringe to maintain a mean BP of 45 tott and mean CO of 30% baseline for one hour. Animals are then resuscitated with the entire volume of shed blood plus lactated Ringer's titrated to restore normal Co. This resuscitation is continued for three hours at which time the catheters are removed during anesthesia (5–10 mg/kg ketamine with local 1% lidocaine).

Animals maintained under standard conditions in cages and are monitored daily for weight, Hct and arterial blood gases. At 5 days post-hemorrhage, the animals are euthanized by pentobarbital overdose and necropsy performed. Organs are examined for gross evidence of injury and histological evidence of injury in tissue sections stained with hematoxylin and eosin.

Animal models of septic and endotoxic shock are described in Thomas et al., 1992 *J. Applied Physiol* 73(4):1510–1516. Using these models, 3 pg/kg to 3 mg/kg doses of SERP-1 are administered to animals prior to and/or following endotoxin infusion or appendectomy daily for three days via intravenous, intramuscular, subcutaneous or intraperitoneal administration. SERP-1 efficacy in preventing shock is monitored in sacrificed animals from days 1 through 5 following endotoxin infusion or appendectomy.

What is claimed is:

1. A method of treating inflammatory arthritis which comprises administering to a mammalian subject having a site of arthritic inflammation, a therapeutically effective amount of SERP-1, SERP-1 analog or biologically active fragment thereof.

2. The method of claim 1, which comprises administering the SERP-1, SERP-1 analog or biologically active fragment thereof at the site of arthritic inflammation.

3. The method of claim 1, which comprises administering to said subject, a therapeutically effective amount of SERP-1, SERP-1 analog or biologically active fragment thereof wherein said SERP-1 has an amino acid sequence comprising (FIG. 1) SEQ ID NO.:1.

4. The method of claim 1, wherein said subject is human.

* * * * *

UNITED STATES PATENT AND TRADEMARK OFFICE
CERTIFICATE OF CORRECTION

PATENT NO.   : 5,939,525
DATED        : August 17, 1999
INVENTOR(S)  : D. G. McFadden It is certified that error appears in the above-identified patent and that said Letters Patent is hereby corrected as shown below:

Column 4,
Line 67, "CDl11b" should read -- CD11b --

Column 8,
Line 48, "Compositions" should read -- compositions --

Column 22,
Line 6, "Nippostronqylus" should read -- Nippostrongylus --

Column 26,
Line 58, "SERP1" should read -- SERP-1 --

Column 27,
Line 1, "Immunoloqy" should read -- Immunology --

Signed and Sealed this

Twenty-sixth Day of March, 2002

Attest:

*Attesting Officer*

JAMES E. ROGAN
*Director of the United States Patent and Trademark Office*